United States Patent
Kutyavin et al.

(10) Patent No.: US 7,252,940 B2
(45) Date of Patent: Aug. 7, 2007

(54) ABASIC SITE ENDONUCLEASE ASSAY

(75) Inventors: Igor V. Kutyavin, Woodinville, WA (US); David Milesi, Seattle, WA (US); Merl F. Hoekstra, Monroe, WA (US)

(73) Assignee: Epoch Biosciences, Inc., Bothell, WA (US)

( * ) Notice: Subject to any disclaimer, the term of this patent is extended or adjusted under 35 U.S.C. 154(b) by 480 days.

(21) Appl. No.: 10/645,353

(22) Filed: Aug. 20, 2003

(65) Prior Publication Data

US 2004/0101893 A1    May 27, 2004

Related U.S. Application Data

(60) Provisional application No. 60/405,642, filed on Aug. 21, 2002.

(51) Int. Cl.
  *C12Q 1/68* (2006.01)
  *C07H 21/02* (2006.01)
  *C07H 21/04* (2006.01)

(52) U.S. Cl. .................. 435/6; 536/23.1; 536/24.3

(58) Field of Classification Search .............. 435/6; 536/23.1, 24.3
  See application file for complete search history.

(56) References Cited

U.S. PATENT DOCUMENTS

| | | | |
|---|---|---|---|
| 4,876,187 A | 10/1989 | Duck et al. | |
| 5,011,769 A | 4/1991 | Duck et al. | |
| 5,403,711 A | 4/1995 | Walder et al. | |
| 5,516,663 A | 5/1996 | Backman et al. | |
| 5,656,430 A | 8/1997 | Chirijian et al. | |
| 5,660,988 A | 8/1997 | Duck et al. | |
| 5,731,146 A | 3/1998 | Duck et al. | |
| 5,747,255 A | 5/1998 | Brenner | |
| 5,763,178 A | 6/1998 | Chirikjian et al. | |
| 5,792,607 A | 8/1998 | Backman et al. | |
| 6,001,610 A | 12/1999 | Seibl et al. | |
| 6,190,865 B1 | 2/2001 | Jendrisak et al. | |
| 6,274,316 B1 | 8/2001 | Modrusan | |
| 6,277,632 B1 | 8/2001 | Harney | |
| 6,309,838 B1 | 10/2001 | Chaubron et al. | |
| 6,340,566 B1 | 1/2002 | McCutchen-Maloney | |
| 6,350,580 B1 | 2/2002 | Sorge | |
| 6,579,680 B2 | 6/2003 | Frutos et al. | |

FOREIGN PATENT DOCUMENTS

WO    WO 99/13108 A1    3/1999
WO    WO 99/54501 A1    10/1999

OTHER PUBLICATIONS

Vaughan et al. A Novel process for mutation detection using uracil DNA glycosylase. Nucleic Acids Reasearch 26(3) : 810-815 (1998).*

Kutyavin, Igor, "3'-Minor groove binder-DNA probes increase sequence specificity at PCR extension temperatures," Nucleic Acids Research, 2000, vol. 28, No. 2, pp. 655-661.

Marras, Salvatore, "Multiplex detection of single-nucleotide variations using molecular beacons," Genetic Analysis: Biomolecular Engineering, 1999, vol. 14, pp. 151-156.

* cited by examiner

*Primary Examiner*—Ethan Whisenant
(74) *Attorney, Agent, or Firm*—Townsend and Townsend and Crew LLP

(57) ABSTRACT

The present invention provides a novel method for detection and/or genotyping of nucleic acids that utilizes the specificity of an AP endonuclease. In addition, the present invention provides a novel method for nucleic acid amplification.

28 Claims, 17 Drawing Sheets

Examples of linkers (covalent binding):

$(-OCH_2CH_2-)_n$ $(-OCH_2CH_2-OPO_2-)_n$ $-O(CH_2)_nO-$  where n is from 1 to 100

SEQUENCE LISTING

<160> NUMBER OF SEQ ID NOS: 17

<210> SEQ ID NO 1
<211> LENGTH: 47
<212> TYPE: DNA
<213> ORGANISM: Artificial Sequence
<220> FEATURE:
<223> OTHER INFORMATION: Description of Artificial Sequence:hairpin
      substrate structure simulating probe-target
      nucleic acid-enhancer complex
<220> FEATURE:
<221> NAME/KEY: modified_base
<222> LOCATION: (47)
<223> OTHER INFORMATION: n = c modified by 3' tail
      2-(6-oxy-2- octylcarbamoyl]-ethyl
-3-oxo-3H-xanthen-9-yl)-benzoate
      (structure #2)

<400> SEQUENCE: 1
gccacattgg aagccaatgt ggcgggcaag gaccgaaggt ccttgcn          47

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence:flexible
      polypeptide chain probe-enhancer linker

<400> SEQUENCE: 2

Gly Ser Ser Ser Ser
 1               5

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:target
      oligonucleotide

<400> SEQUENCE: 3
aatgtggcgg gcaaggaccg agtc                                         24

<210> SEQ ID NO 4
<211> LENGTH: 11
<212> TYPE: DNA
<213> ORGANISM: Artificial Sequence
<220> FEATURE:
<223> OTHER INFORMATION: Description of Artificial Sequence:11-mer probe
      complementary to target oligonucleotide
<220> FEATURE:
<221> NAME/KEY: modified_base
<222> LOCATION: (1)
<223> OTHER INFORMATION: n = a modified by 5' conjugated quencher
      phosphoric acid 1-(4- phenyl]-methyl-amino
-butyryl)-5-hydroxymethyl-pyrrolidin-
      3-yl ester methyl ester (structure #15)
<220> FEATURE:
<221> NAME/KEY: modified_base
<222> LOCATION: (11)
<223> OTHER INFORMATION: n = t modified by 3' tail of fluorescein (FAM)
      and linker 4,5-dichloro-2-(4,7-dichloro-6-oxy-2-

(oxy-methoxy-phosphoryloxymethyl)-pyrrolidin-1-yl]-3-oxo-propyl
-
      5-methyl-3-oxo-3H-xanthen-9-yl)-benzoate (structure #8)

<400> SEQUENCE: 4
nctcggtcct n                                                       11

<210> SEQ ID NO 5
<211> LENGTH: 11
<212> TYPE: DNA
<213> ORGANISM: Artificial Sequence
<220> FEATURE:
<223> OTHER INFORMATION: Description of Artificial Sequence:enhancer
      oligonucleotide for 1 base gap between target
      oligonucleotide and duplexes of probe and enhancer

<400> SEQUENCE: 5
cccgccacat t                                                       11

<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence:enhancer
      oligonucleotide for 0 base gap between target
      oligonucleotide and duplexes of probe and enhancer

<400> SEQUENCE: 6
gcccgccaca t                                                       11

<210> SEQ ID NO 7
<211> LENGTH: 10
<212> TYPE: DNA
<213> ORGANISM: Artificial Sequence
<220> FEATURE:

-continued

```
<223> OTHER INFORMATION: Description of Artificial Sequence:enhancer
      oligonucleotide for 2 base gap between target
      oligonucleotide and duplexes of probe and enhancer

<400> SEQUENCE: 7
ccgccacatt                                                            10

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence:41-mer fully
      matched DNA target sequence

<400> SEQUENCE: 8
agtcacagtc ggtgccaatg tggcgggcaa ggaccgagtc g                         41

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence:enhancer
      oligonucleotide

<400> SEQUENCE: 9
gccacattgg caccgactgt ga                                              22

<210> SEQ ID NO 10
<211> LENGTH: 14
<212> TYPE: DNA
<213> ORGANISM: Artificial Sequence
<220> FEATURE:
<223> OTHER INFORMATION: Description of Artificial Sequence:14-mer
      oligonucleotide probe
<220> FEATURE:
<221> NAME/KEY: modified_base
<222> LOCATION: (1)
<223> OTHER INFORMATION: n = a modified by 5' conjugated quencher
      phosphoric acid 1-(4- phenyl]-methyl-amino
-butyryl)-5-hydroxymethyl-pyrrolidin-
      3-yl ester methyl ester (structure #15)
<220> FEATURE:
<221> NAME/KEY: modified_base
<222> LOCATION: (14)
<223> OTHER INFORMATION: n = t modified by 3' tail of fluorescein (FAM)
      and linker 4,5-dichloro-2-(4,7-dichloro-6-oxy-2-

(oxy-methoxy-phosphoryloxymethyl)-pyrrolidin-1-yl]-3-oxo-propyl
-
      5-methyl-3-oxo-3H-xanthen-9-yl)-benzoate (structure #8)

<400> SEQUENCE: 10
nctcggtcct tgcn                                                       14

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence:10-mer
      oligonucleotide probe
<220> FEATURE:
<221> NAME/KEY: modified_base
<222> LOCATION: (1)
<223> OTHER INFORMATION: n = a modified by 5' conjugated quencher
      phosphoric acid 1-(4-
```

```
        phenyl]-methyl-amino
        -butyryl)-5-hydroxymethyl-pyrrolidin-
        3-yl ester methyl ester (structure #15)
<220>   FEATURE:
<221>   NAME/KEY: modified_base
<222>   LOCATION: (10)
<223>   OTHER INFORMATION: n = t modified by 3' tail of fluorescein (FAM)
        and linker 4,5-dichloro-2-(4,7-dichloro-6-oxy-2-
        (oxy-methoxy-phosphoryloxymethyl)-pyrrolidin-1-yl]-3-oxo-propyl
        5-methyl-3-oxo-3H-xanthen-9-yl)-benzoate (structure #8)

<400>   SEQUENCE: 11 ngtccttgcn                                                              10

<210>   SEQ ID NO 12
<211>   LENGTH: 27
<212>   TYPE: DNA
<213>   ORGANISM: Artificial Sequence
<220>   FEATURE:
<223>   OTHER INFORMATION: Description of Artificial Sequence:fragment of
        target sequence around single nucleotide
        polymorphism in human genomic DNA

<400>   SEQUENCE: 12 aaagagacac ggacayatca atccatc                                           27

<210>   SEQ ID NO 13
<211>   LENGTH: 20
<212>   TYPE: DNA
<213>   ORGANISM: Artificial Sequence
<220>   FEATURE:
<223>   OTHER INFORMATION: Description of Artificial Sequence:asymmetric
        PCR amplification forward primer

<400>   SEQUENCE: 13 caaactttgt ccttggtcta                                                   20

<210>   SEQ ID NO 14
<211>   LENGTH: 20
<212>   TYPE: DNA
<213>   ORGANISM: Artificial Sequence
<220>   FEATURE:
<223>   OTHER INFORMATION: Description of Artificial Sequence:asymmetric
        PCR amplification reverse primer

<400>   SEQUENCE: 14 ttcttttacc actccccctt                                                   20

<210>   SEQ ID NO 15
<211>   LENGTH: 13
<212>   TYPE: DNA
<213>   ORGANISM: Artificial Sequence
<220>   FEATURE:
<223>   OTHER INFORMATION: Description of Artificial Sequence:
        complementary target oligodeoxyribonucleotide (ODN)

<400>   SEQUENCE: 15 caaggaccga gtc                                                          13

<210>   SEQ ID NO 16
<211>   LENGTH: 11
<212>   TYPE: DNA
<213>   ORGANISM: Artificial Sequence
<220>   FEATURE:
<223>   OTHER INFORMATION: Description of Artificial
        Sequence:oligodeoxyribonucleotide (ODN) probe
<220>   FEATURE:
```

```
<221> NAME/KEY: modified_base
<222> LOCATION: (1)
<223> OTHER INFORMATION: n = a modified by 5' conjugated quencher
      phosphoric acid 1-(4- phenyl]-methyl-amino
-butyryl)-5-hydroxymethyl-pyrrolidin-
      3-yl ester methyl ester (structure #15)
<220> FEATURE:
<221> NAME/KEY: modified_base
<222> LOCATION: (11)
<223> OTHER INFORMATION: n = t modified by 3' tail of fluorescein (FAM)
      and linker 4,5-dichloro-2-(4,7-dichloro-6-oxy-2-

(oxy-methoxy-phosphoryloxymethyl)-pyrrolidin-1-yl]-3-oxo-propyl
-
      5-methyl-3-oxo-3H-xanthen-9-yl)-benzoate (structure #8)

<400> SEQUENCE: 16
nctcggtcct n                                                          11

<210> SEQ ID NO 17
<211> LENGTH: 11
<212> TYPE: DNA
<213> ORGANISM: Artificial Sequence
<220> FEATURE:
<223> OTHER INFORMATION: Description of Artificial
      Sequence:oligodeoxyribonucleotide (ODN) probe
<220> FEATURE:
<221> NAME/KEY: modified_base
<222> LOCATION: (1)
<223> OTHER INFORMATION: n = a modified by 5' conjugated quencher
      phosphoric acid 1-(4- phenyl]-methyl-amino
-butyryl)-5-hydroxymethyl-pyrrolidin-
      3-yl ester methyl ester (structure #15)

<400> SEQUENCE: 17
nctcggtcct t                                                          11
```

ABASIC SITE ENDONUCLEASE ASSAY

CROSS-REFERENCES TO RELATED APPLICATIONS

This application claims the benefit of provisional application Ser. No. 60/405,642, filed on Aug. 21, 2002, the disclosure of which is hereby incorporated herein by reference in its entirety.

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK.

NOT APPLICABLE

BACKGROUND OF THE INVENTION

Apurinic/Apyrimidinic (AP), or abasic, sites arise spontaneously in DNA with a calculated rate up to 10,000 bases per human cell per day. AP sites are cytotoxic and mutagenic and need to be repaired quickly in order to maintain the functional and genetic integrity of the genome. One of the major sources of AP sites is inherent instability of the glycosylic bond, found predominantly in purines. Abasic sites can also arise either by the actions of reactive oxygen species, or by enzymatic excision of damaged bases via the cleavage of the N-glycosyl bond catalyzed by a DNA glycosylase (See: Prokaryotic Base Excision Repair, Wilson III, D. M., Engelward, B. P. and Samson, L. (1998) pp.29-64; from: DNA Damage and Repair, V.1: DNA Repair in Prokaryotes and Lower Eukaryotes, Edited by: J. A. Nickoloff and M. F. Hoekstra, humana Press Inc., Totowa, N.J.).

AP sites in double-stranded DNA are recognized by a class of enzymes termed Class II AP endonucleases that cleave the phosphodiester backbone on the 5' side of the AP site via a hydrolytic mechanism, thereby providing a free 3'-OH group that serves as a substrate for DNA polymerases to initiate Base Excision Repair (BER). The Endonuclease IV from *Escherichia coli* is one example of a Class II AP endonuclease. See: Regulation of Endonuclease IV as Part of an Oxidative Stress Response in *Escherichia coli*, Weiss B. (1998) pp.85-96; from: DNA Damage and Repair, V.1: DNA Repair in Prokaryotes and Lower Eukaryotes, Edited by: J. A. Nickoloff and M. F. Hoekstra, humana Press Inc., Totowa, N.J.

A number of DNA glycosylases that are called Class I AP endonucleases exhibit AP site-cleavage activity as part of their mechanism of action. However, these enzymes act as β-elimination catalysts, cleaving the phosphodiester backbone 3' to the AP site, resulting in atypical 3'-termini, such as 3'-phosphoglycolate and 3'-phosphate. These atypical termini block the 3'-OH group that serve as a substrate for polymerases and are subject to subsequent repair by the Class II AP endonucleases that cleave the blocks and initiate the BER. See: Prokaryotic Base Excision Repair, Wilson III, D. M., Engelward, B. P. and Samson, L. (1998) pp.29-64; from: DNA Damage and Repair, V.1: DNA Repair in Prokaryotes and Lower Eukaryotes, Edited by: J. A. Nickoloff and M. F. Hoekstra, humana Press Inc., Totowa, N.J.; and Abasic Site Repair in Higher Eukaryotes, Strauss, P. R. and O'Regan, N. E. (2001) pp.43-86; from: DNA Damage and Repair, V.3: Advances from Phage to Human, Edited by: J. A. Nickoloff and M. F. Hoekstra, humana Press Inc., Totowa, N.J.

Polynucleotide identification assays that are based on a selective cleavage of a probe hybridized to a target nucleic acid have been disclosed by others. For example, U.S. Pat. Nos. 4,876,187; 5,011,769; 5,660,988; 5,731,146; 5,747,255 and 6,274,316 disclose nucleic acid probes having a scissile linkage incorporated as part of the nucleic acid backbone and in the middle of the nucleic acid probe. U.S. Pat. No. 5,403,711 also discloses a similarly designed DNA-RNA-DNA probe, wherein the embedded RNA sequence is a substrate for RNase H when duplexed. Hybridized probes with an incorporated cleavable linkage within the middle of the probe have a diminished duplex stability after the enzymatic cleavage. Their cleavable sites also are not exquisitely specific.

U.S. Pat. Nos. 5,516,663 and 5,792,607 disclose using endonuclease IV to remove an abasic site incorporated as a blocking agent on the 3' end of an oligonucleotide to improve specificity and sensitivity of the ligase chain reaction (LCR) or polymerase chain reaction (PCR) amplification.

U.S. Pat. Nos. 5,656,430; 5,763,178; 6,340,566 disclose methods for detecting point mutations by using an endonuclease to cleave the nucleic acid backbone in the middle of the oligonucleotide at the point of mutation. In methods that identify a mismatch by enzymatic cleavage of a nucleic acid backbone, the presence, rather than the absence, of a mismatch stimulates the cleavage of the probe phosphodiester backbone.

U.S. Pat. No.6,309,838 discloses using labeled nucleotide excision repair enzymes to detect bound enzyme to DNA sequence impairments.

European Patent EP 1 071 811 B1 discloses a method of DNA synthesis from a 3'-OH generated by cleavage with a DNA glycosylase, but this method requires the steps of introducing a modified base and excising the modified base with a glycosylase followed with a treatment by AP endonuclease before carrying out the extension.

What is needed in the art is an assay which combines the advantages of target nucleic acid cycling, retained binding stability of the probe, an exquisitely specific cleavage site, the possibility for essentially instantaneous and highly sensitive reporter detection and the ability to directly combine detection with amplification procedures. Accordingly, there remains a need for compositions and methods that enable efficient detection of target nucleic acids with exquisite specificity. The present invention fulfills this need and others.

BRIEF SUMMARY OF THE INVENTION

Provided is an AP site probe comprised of an oligonucleotide NA that hybridizes to a target nucleic acid, and a functional tail R comprising a detectable reporter group and an AP endonuclease cleavage site attached through a phosphodiester bond of a phosphate group to the 3' terminal nucleotide of the NA, wherein the reporter group is not detected when the functional, chemical tail R is attached to the NA.

The AP site probes find use in methods and assays for detecting a target nucleic acid of interest in a sample. The methods involve contacting the sample with at least one AP site probe and an AP endonuclease, under reaction conditions sufficient to allow the at least one AP site probe to hybridize to the target nucleic acid and form a reaction mixture, incubating the reaction mixture under reaction conditions that allow the AP endonuclease to cleave the phosphodiester bond attaching the functional tail R to the 3' terminal nucleotide of the NA, and detecting the reporter group on the cleaved functional tail R. The methods are exquisitely sensitive to the detection of single base pair mismatches between a probe NA component and a target nucleic acid because the AP endonuclease preferentially cleaves the phosphodiester bond attaching the tail R to the NA when the NA is hybridized with a fully complementary nucleic acid sequence in comparison to cleaving a functional tail attached to a NA that is unhybridized or hybridized to a non-complementary nucleic acid.

The invention further provides primers with internal AP endonuclease-cleavable sites (pL), the primers having a sequence structure $(NA_1-L)_m-NA_2$, wherein $NA_1$ and $NA_2$ are nucleic acid sequences complementary to the target nucleic acid, L is an AP endonuclease-cleavable linker, and m is from 0 to 100, where at least one of the forward primer and the reverse primer comprises an AP endonuclease-cleavable linker, L. The primers find use in methods for amplifying a target nucleic acid sequence of interest in a sample, the methods involving contacting a sample with at least one forward and at least one reverse primer having internal AP endonuclease-cleavable sites, an AP endonuclease, and a nucleic acid polymerase, under conditions sufficient to allow the forward and reverse primers to hybridize to the target nucleic acid and form a reaction mixture, and incubating the reaction mixture under reaction conditions that simultaneously allow the AP endonuclease to cleave at a linker site L, thereby generating a free 3'-OH, and the polymerase to extend the primers in a template-specific manner.

The invention further contemplates kits containing reagents, including at least one AP site probe, for carrying out the described methods.

DETAILED DESCRIPTION OF THE INVENTION

I. General

Figure 1:
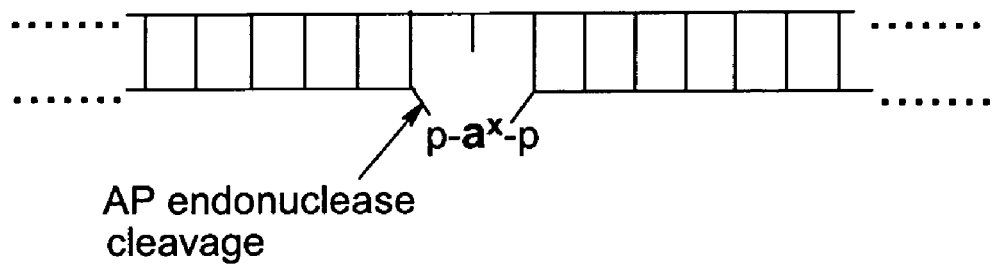
FIG. 1 illustrates the structure of two types of DNA lesions cleaved by AP endonucleases. "$a^x$" represents an abasic site, 2'-deoxyribose. "s" represents products of the 2'-deoxyribose (abasic site). Spontaneous or enzymatic degradation leads to cleavage of the phosphodiester bond between the 3'-hydroxyl group of the ribose (abasic site) and the nearest nucleotide of the DNA strand. Lesion 1 is a typical AP, or abasic, site generated by loss of a nuclear base. Lesion 2 is an atypical abasic site that appears as a result of inherent instability of the deoxyribose in Lesion 1 or its cleavage by a Class I AP endonuclease.
Figure 1:
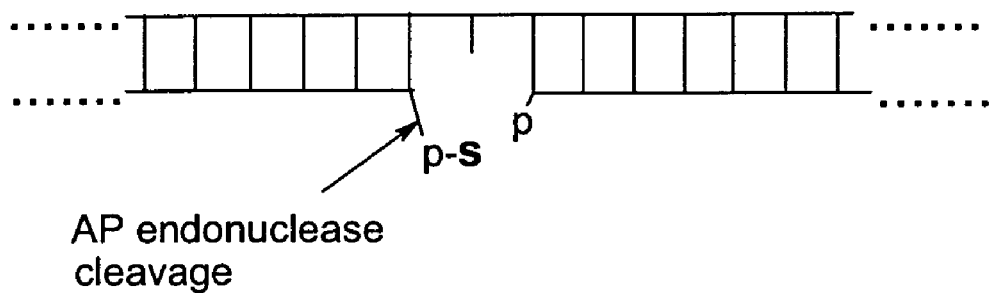

The present invention provides assay methods that combine the advantages of nucleic acid cycling despite the retained binding stability of the probe after tail cleavage, an exquisitely target-specific enzymatic cleavage reaction, the possibility for essentially instantaneous and highly sensitive reporter detection and the ability to directly combine detection with amplification procedures without requiring additional primers, additional enzymes other than a polymerase or other additional steps.

II. Definitions

As used herein, an AP site probe is a nucleic acid probe comprised of an oligonucleotide sequence NA attached at its 3' end to a phosphodiester bond of a phosphate group, to a functional, chemical tail R comprising an AP endonuclease cleavage site and a functional group. In preferred embodiments, the phosphate group is linked to the functional, chemical tail through a hydroxyprolinol linker. The functional group can be a reporter or a quencher group.

An abasic site is an naturally occurring Apurinic/Apyrimidinic (AP) site in a nucleic acid sequence or a synthetic linker that is recognized and cleaved by Class II AP endonucleases when it appears in double stranded DNAs.

As used herein, an AP endonuclease refers to an enzyme that binds to and cleaves the phosphodiester backbone at an abasic (AP) site on a nucleic acid strand in a double stranded DNA. Preferred AP endonucleases cleave the phosphodiester backbone on the 5' side of the AP site via a hydrolytic mechanism that provides a free 3'-OH group that serves as a substrate for DNA polymerases.

By "duplex" is intended two hybridized nucleic acid strands. A probe duplexed to a target nucleic acid, can alternately be said to be hybridized to the target nucleic acid.

III. DESCRIPTION OF THE EMBODIMENTS

The present invention provides an AP site probe comprised of an oligonucleotide NA that hybridizes to a target nucleic acid, and a functional tail R comprising a detectable reporter group and an AP endonuclease cleavage site linked via a phosphodiester bond of a phosphate group to the 3' terminal nucleotide nucleotide of the NA, wherein the reporter group is not detected when the functional, chemical tail R is attached to the NA. The AP endonuclease preferentially cleaves the functional tail R when the NA component is hybridized to a complementary target nucleic acid, such that its cleavage by an AP endonuclease results in a free 3'-OH group. In a preferred embodiment, the functional tail R is linked to the NA terminal 3' phosphate group via a hydroxyprolinol linker. In a preferred embodiment, the reporter group is a fluorophore. In some embodiments, an AP site probe will further have a quencher or quenching molecule attached to its 5'-end via an AP endonuclease non-cleavable linker.

In some embodiments, the NA portion of the AP site probe comprises one or more modified bases. In some embodiments, the NA portion of the AP site is a member of a universal library, usually of about 5, 6, 7 or 8 nucleotides in length. In some embodiments, the NA portion of the AP site probe is a member of a universal library comprising at least one modified base.

In an alternative embodiment, the functional tail R attached to the 3'-end of the AP site probe comprises a quencher molecule attached through an AP endonuclease-cleavable linker and a detectable reporter group moiety that is attached via an AP endonuclease non-cleavable linker to the 5'-end of the probe.

One or more AP site probes find use in methods and assays for detecting a target nucleic acid of interest in a sample. The methods involve (i) contacting the sample with at least one AP site probe and an AP endonuclease, preferably a Class II AP endonuclease, under reaction conditions sufficient to allow the at least one AP site probe to hybridize to the target nucleic acid and form a reaction mixture, (ii) incubating the reaction mixture under reaction conditions that allow the AP endonuclease to cleave the phosphodiester bond attaching the functional tail R to the 3' terminal nucleotide of the NA, and (iii) detecting the reporter group on the cleaved functional tail R. The methods allow for cycling of the target nucleic acid while still preserving a stable hybridization complex between the NA component of the AP site probe and the target nucleic acid before and after cleavage of the functional tail R by the AP endonuclease.

The methods are exquisitely sensitive to the detection of single base pair mismatches between a probe NA component and a target nucleic acid because the AP endonuclease preferentially cleaves the phosphodiester bond attaching the tail R to the NA when the NA is hybridized with a complementary nucleic acid sequence in comparison to cleaving a functional tail attached to a NA that is unhybridized or hybridized to a non-complementary nucleic acid. Usually, when carrying out a method of discriminating mismatches between one or more base pairs, the target nucleic acid sample is contacted with a first AP site probe and a second AP site probe, where the NA component of the first probe has at least one base difference from the NA component of the second probe, and where the first probe has a reporter group that is distinguishably detectable from the reporter group of the second probe. Preferably, the reporter groups of the first and second probe comprise a fluorophore, where the fluorophore of the first probe has a distinguishably detectable emission wavelength from the fluorophore of the second probe. Mismatch discrimination is particularly sensitive when the mismatch is located at positions 1 or 2 bases from the 3'-end of the NA component of an AP site probe. More than two AP site probes can be applied in the same reaction mixture to detect the target polymorphism. Those skilled in the art would appreciate that these AP site probes would carry distinguishable detection markers.

Usually, the target nucleic acid in a sample is further contacted with an enhancer oligonucleotide, where the 5'-end of the enhancer oligonucleotide hybridizes to the target nucleic acid on the 3' side of the hybridized AP site probe, leaving a gap of 0-2 unpaired bases between the enhancer-target and probe-target duplexes. The most preferred gap is one base. In some embodiments, the AP site probe and the enhancer oligonucleotide are attached to each other through a linker molecule.

In some embodiments, either the target nucleic acid, the enhancer or the AP site probe are attached to a solid support. The attachment may be either through a covalent linkage or through non-covalent interactions.

The methods for detecting a target nucleic acid of interest are particularly suited for combining with methods of polymerase extension of primers hybridized to the target nucleic acid. Procedures for primer extension can be carried out before or during procedures for detection. In a preferred embodiment primer extension and detection can be executed directly after endonuclease cleavage. Because cleavage of the phosphodiester bond of the functional tail R results in a hybridized NA having a free 3-OH substrate, primer extension involves further adding a polymerase and NTPs to the sample and incubating the sample under reaction conditions that allow the polymerase to extend the hybridized NA in a template-specific manner. The methods for detecting a target nucleic acid of interest by target-specific cleavage of the AP site probes are particularly suited for combining with methods of target amplification. Target detection can be carried out during (real-time) or after procedures for amplification. In one embodiment the AP site probe cleavage detection can be executed directly after the target amplification. In another embodiment the detection can be executed during the target amplification. In alternative embodiments, target amplification is isothermal amplification or polymerase chain reaction amplification.

The invention further provides primers with internal AP endonuclease-cleavable sites (pL), the primers having a sequence structure $(NA_1-L)_m-NA_2$, wherein $NA_1$ and $NA_2$ are nucleic acid sequences complementary to the target nucleic acid, L is an AP endonuclease-cleavable linker, and m is from 0 to 100. The primers find use in methods for amplifying a target nucleic acid sequence of interest in a sample, the methods involving contacting a sample with at least one forward and at least one reverse primer having internal AP endonuclease-cleavable sites, an AP endonuclease, a nucleic acid polymerase and NTPs, under conditions sufficient to allow the forward and reverse primers to hybridize to the target nucleic acid and form a reaction mixture, and incubating the reaction mixture under reaction conditions that simultaneously allow the AP endonuclease to cleave at a linker site L, thereby generating a free 3'-OH, and the polymerase to extend the primers in a template-specific manner. The target nucleic acid can be amplified by either isothermal amplification or polymerase chain reaction.

The invention further provides kits containing reagents, including at least one AP site probe, for carrying out the claimed methods. In kits containing reagents for detecting at least one single nucleotide polymorphism, sets of 1 to 4 AP site probes are included for each polymorphism location. Each AP site probe in a set will have a reporter group that is distinguishably detectable from the other AP site probe reporter groups in the set intended to discriminate one or more polymorphisms at a particular location on a target nucleic acid.

A. Target Nucleic Acid

Probes comprising a nucleic acid, an AP site and a functional tail are useful for the detection of single-stranded nucleic acids ("ssNA") and double-stranded nucleic acids ("dsNA"). When used for the detection of double-stranded nucleic acids, unless the population of dsNA contains a sufficient amount of ssNA to be detected using an AP site probe, the dsNA is prepared to provide a sufficient amount of ssNA. Ordinarily, the dsNA is melted or denatured at an elevated temperature prior to their detection. Also, dsNA can be prepared such that a fragment of the target nucleic acids to which the probe and enhancer are complimentary is single-stranded while the rest of the target is double-stranded. Single-stranded target nucleic acids can be isolated from the double-stranded forms using available molecular biology or physicochemical methods, including strand-specific enzymatic degradation, limited digestion of the double-stranded target followed by heat treatment, or affinity capture through a sequence-incorporated affinity label followed by heat-induced separation from the complementary strand.

Target nucleic acids can be isolated from a variety of natural sources, including blood, homogenized tissue, fixed tissue, tumor biopsies, stool, clinical swabs, food products, hair, plant tissues, microbial culture, public water supply, amniotic fluid, urine, or the like. Techniques useful for the isolation of target nucleic acids include, for example, amplification techniques, e.g., polymerase chain reaction (PCR), Mullis, U.S. Pat. No. 4,683,202; ligase-based techniques, e.g., reviewed by Barany, PCR Methods and Applications 1: 5-16 (1991); strand-displacement amplification, Walker et al., U.S. Pat. No. 5,422,252; reverse transcriptase-based techniques, e.g., Davey et al., U.S. Pat. No. 5,409,818; Q.beta. replicase-based techniques, e.g., Chu et al., U.S. Pat. No. 4,957,858; branched DNA techniques, Urdea et al., U.S. Pat. No. 5,124,246; techniques employing RNA-DNA chimeric probes, Duck et al., U.S. Pat. No. 5,011,769; and the like.

Samples containing target nucleic acids can be isolated from natural sources or provided as result of any known method in the art. The target nucleic acid can be cloned, synthetic, or natural. The target nucleic acid can be deoxyribonucleic acid (DNA), including genomic DNA or cDNA, or ribonucleic acid (RNA). Usually a DNA target nucleic acid is preferred. Target nucleic acids can be of diverse origin, including mammalian, bacterial, fungal, viral, or plant origin. The need for extraction, purification, or isolation steps depends on several factors, including the abundance of the target nucleic acids in the sample, the nature of the target nucleic acids, e.g., whether it is RNA or DNA, the presence of extraneous or associated material such as cell walls, histones, or the like, the presence of enzyme inhibitors, and so forth.

Guidance for selecting an appropriate protocol for particular applications for extraction, purification and/or isolation of target nucleic acids can be found in, for example, Chen and Janes, Editors, PCR Cloning Protocols (Humana Press, Totowa, N.J., 2002); Sambrook et al., Molecular Cloning, Second Edition (Cold Spring Harbor Laboratory Press, 2001); White, Editor, PCR Cloning Protocols: from molecular cloning to genetic engineering (Humana Press, Totowa, N.J., 1997); Methods in Enzymology, Volumes 6 and 12, parts A and B (Academic Press, New York); McPherson et al., Editors, PCR: A Practical Approach (IRL Press, Oxford, 1991); Herrington et al., Editors, Diagnostic Molecular Pathology: A Practical Approach, Vol. 1 & 2 (IRL Press, Oxford, 1992); Innis, et al., Editors, PCR Protocols (Academic Press, San Diego, 1990); and the like. Typically, preparation protocols involve the application of chaotropic agents, for example, low molecular weight ionic compounds, that favor the solubilization of hydrophobic substances, chelating agents (for instance, EDTA), to disable nucleases, proteases to disable nucleases, detergents, pH buffers, and the like, that serve to isolate and/or protect nucleic acids. Optionally, samples can be treated to reduce the size of the target nucleic acids, such as by sonication, nuclease treatment, or the like. After such initial preparation steps, preferably a sample is treated to denature, i.e. render single-stranded, the target polynucleotide prior to exposing it to the nucleic acid probe, enhancer and AP endonuclease in accordance with the invention. Preferably, denaturation is achieved by heating the sample at 93-95° C. for five minutes.

In assays of the present invention, a target nucleic acid is typically included in concentrations of about 2-10 nM, more typically about 4-8 nM, and preferably at a concentration of about 5 nM. However, one of skill in the art will appreciate that the invention is not so limited and other concentrations of target can also be used, whether higher or lower than those indicated above.

B. AP Site Probe

Generally, the structure of an AP site probe is as follows:

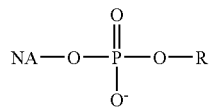

An AP site probe is comprised of a nucleic acid ("NA") covalently bound by its 3'-terminal oxygen atom to a functional, chemical tail ("R") through a phosphodiester group.

1. Nucleic Acid Component of Probe

The number of nucleotides in the NA component can be 3 to 200, 3 to 100 or 3 to 200 nucleotides in length, depending on the intended use. Usually, the length of the NA is from 5 to 30 nucleotides. More typically, the length of the NA is 6-25, 7-20, or 8-17 nucleic acids. Most often, the NA component is about 6, 7, 8, 9, 10, 11, 12, 13, 14, 15 or 16 nucleic acids in length. Usually, the NA component will have a hybridization melting temperature of about 10 to 80° C., more typically of about 20 to 70° C., and preferably about 30° C., 40° C., 50° C. or 60° C.

The sugar, or glycoside, portion of the NA component of the conjugates can comprise deoxyribose, ribose, 2-fluororibose, and/or 2-O-alkyl or alkenylribose wherein the alkyl group comprises 1 to 6 carbon atoms and the alkenyl group comprises 2 to 6 carbon atoms. In the naturally-occurring nucleotides, modified nucleotides and nucleotide analogues that can comprise an oligonucleotide, the sugar moiety forms a furanose ring, the glycosidic linkage is of the beta configuration, the purine bases are attached to the sugar moiety via the purine 9-position, the pyrimidines via the pyrimidine 1-position and the pyrazolopyrimidines via the pyrazolopyrimidine 1-position (which is equivalent to the purine 9-position). In a preferred embodiment, the sugar moiety is 2-deoxyribose; however, any sugar moiety known to those of skill in the art that is compatible with the ability of the oligonucleotide portion of the compositions of the invention to hybridize to a target sequence can be used.

In one preferred embodiment, the NA is DNA. An AP site probe comprising DNA can be used to detect DNA, as well as RNA, targets. In another embodiment, the NA is RNA. An AP site probe comprising RNA is generally used for the detection of target DNAs. In another embodiment, an AP site probe can contain both DNA and RNA distributed within the probe. In mixed nucleic acid probes, DNA bases preferably are located at 3'-end of the probe while RNA bases are at the 5'-end. It is also preferred when the 3'-terminal nucleotide is 2'-deoxyribonucleotide (DNA) and when at least four 3'-terminal bases of NA are DNA bases.

Usually, the NA component contains the major heterocyclic bases naturally found in nucleic acids (uracil, cytosine, thymine, adenine and guanine). In some embodiments, the NA contains nucleotides with modified, synthetic or unnatural bases, incorporated individually or multiply, alone or in combination. Preferably, modified bases increase thermal stability of the probe-target duplex in comparison with probes comprised of only natural bases (i.e., increase the hybridization melting temperature of the probe duplexed with a target sequence). Modified bases include naturally-occurring and synthetic modifications and analogues of the major bases such as, for example, hypoxanthine, 2-aminoadenine, 2-thiouracil, 2-thiothymine, inosine, 5-$N^4$-ethenocytosine, 4-aminopyrrazolo[3,4-d]pyrimidine and 6-amino-4-hydroxy-[3,4-d]pyrimidine. Any modified nucleotide or nucleotide analogue compatible with hybridization of an AP site probe with a target nucleic acid conjugate to a target sequence is useful in the practice of the invention, even if the modified nucleotide or nucleotide analogue itself does not participate in base-pairing, or has altered base-pairing properties compared to naturally-occurring nucleotides. Examples of modified bases are disclosed in U.S. Pat. Nos. 5,824,796; 6,127,121; 5,912,340; and PCT Publications WO 01/38584; WO 01/64958, each of which is hereby incorporated herein by reference in its entirety. Preferred modified bases include 5-hydroxybutynyl uridine for uridine; 4-(4,6-Diamino-1H-pyrazolo[3,4-d]pyrimidin-3-yl)-but-3-yn-1-ol, 4-amino-1H-pyrazolo[3,4-d]pyrimidine, and 4-amino-1H-pyrazolo[3,4-d]pyrimidine for adenine; 5-(4-Hydroxy-but-1-ynyl)-1H-pyrimidine-2,4-dione for thymine; and 6-amino-1H-pyrazolo[3,4-d]pyrimidin-4(5H)-one for guanine. Particularly preferred modified bases are "Super A™," "Super G™: 4-hydroxy-6-amino pyrazolopyrimidine" (www.Epochbio.com) and "Super T™". Modified bases preferably support the geometry of a naturally occurring B-DNA duplex. Modified bases can be incorporated into any position or positions in an AP site probe, but preferably are not incorporated as the 3'-terminal base.

In another embodiment, some or all nucleotides of NA are substituted or contain independently different sugar-phosphate backbone modifications including 2'-O-alkyl RNA nucleotides, phosphorotioate internucleotide linkage, methylphosphonate, sulfamate (e.g., U.S. Pat. No. 5,470,967) and polyamide (i.e., peptide nucleic acids, PNA), LNA (locked nucleic acid), and the like. Such modifications and others of potential use in the present invention are described, for example, in Boutorine, et al., *Biochimie* 76:23 (1994); Agrawal, et al., *Proc. Natl. Acad. Sci.* 88:7595 (1991); Mag, et al., *Nucleic Acids Res.* 19:1437 (1991); Kurreck, *Eur. J Biochem.* 270:1628 (2003); Lesnik, et al., *Biochemistry* 32:7832 (1993); Sproat, et al., *Nucleic Acids Symp. Ser.* 24:59 (1991); Iribarren, et al., *Proc. Natl. Acad. Sci.* 87:7747 (1990); Demidov, *Trends Biotechnol.* 21:4 (2003); Nielsen, *Methods Mol. Biol.* 208:3 (2002); Nielsen and Egholm, *Curr. Issues Mol. Biol.* 1:89 (1999); Micklefield, *Curr. Med. Chem.* 8:1157 (2001); Braasch, et al., *Chem. Biol.* 8:1 (2001); and Nielsen, *Curr. Opin. Biotechnol.* 12:16 (2001).

Within the scope of present invention, modifications of the bases and sugar-phosphate backbone as well as other functional moieties conjugated with the probe can serve to improve the sequence specificity of the target-probe duplex formation. In particular, binding between the probe and a matched target nucleic acid is detectably increased over binding to a mismatched target nucleic acid. By "matched target nucleic acid" is intended a target nucleic acid that contains a sequence that is completely complimentary to the probe sequence. By "mismatched target nucleic acid" is intended a polynucleotide that contains a sequence that is partially complimentary to the probe sequence such that it contains at least one mismatched, non-complimentary base, deletion or insertion in comparison to the probe sequence. For example, use of modified bases in an AP site probe allows for more stable base pairs than when using natural bases and enables the use of shorter probes for the same reaction conditions. Reduction of the probe length increases the ability of the probe to discriminate a target polymorphism as small as a Single Nucleotide Polymorphism ("SNP") due to a proportional increase in the contribution of each duplex base pair to the overall duplex stability. In general, the shorter the probe, the greater the relative contribution of an individual base pair in to the overall duplex stability, and the better the probe discrimination of the target polynucleotide polymorphism.

2. Functional Tail ("R") Component of Probe

The functional tail R enables detection of the endonuclease tail-cleavage reaction. The structure of R can be of any size and composition as long as it supports the template-specific, endonuclease tail-cleavage reaction. R can be as large as a natural protein with molecular mass up to 1,000,000 Daltons or it can be as small as a single atom (i.e., a radioactive isotope, such as a hydrogen or an iodine). Since the enzymatic hydrolysis occurs between the 3'-terminal oxygen atom of the NA and the phosphorus atom of the phosphodiester bond, for the purposes of the present invention, the phosphate moiety of the probe is considered a part of the functional tail R. For example, when R is hydrogen (R=H), the functional tail of the probe is a phosphate moiety —P(O)(OH)$_2$ or —PO$_3^{2-}$. The tail R can be hydrophobic or hydrophilic, electrically neutral, positively or negatively charged. It can be comprised of or include independently different functional groups, including mass tags, fluorescent or non-fluorescent dyes, linkers, radioisotopes, functional ligands like biotin, oligopeptides, carbohydrates and the like. For example, as demonstrated herein, Endonuclease IV from *E. coli* efficiently cleaves from the 3'-end of a probe bound to the target nucleic acid a relatively hydrophilic, negatively charged fluorescein moiety as well as an electrically neutral, hydrophobic quenching dye.

The tail R can contain components that improve specificity by blocking non-specific cleavage reactions in the absence of a target molecule without affecting the target-dependent, specific reaction. It is also within the scope of present invention that the tail R or some structural components of it can improve the specificity of the target-probe or enhancer-probe complementary binding so that the thermodynamic difference in the probe/enhancer binding to matched and mismatched target nucleic acids is increased. Examples of such structural components are minor groove binders (MGBs).

The functional tail R can incorporate mono-, oligo- or polynucleotides. Nucleotide residues introduced into the tail structure are not intended to bind to the target nucleic acid.

In addition to a functional chemical tail R conjugated to the 3'-end of an AP site probe through a phosphodiester group, the probe optionally can contain other tails and functional moieties covalently attached to the probe or the tail via an appropriate linker. Preferably, the additional moieties do not interfere with endonuclease recognition of the AP tail-cleavage site or the template-specific tail-cleavage reaction. In one embodiment, additional moieties are attached to the 5'-end of the NA portion of the probe. In another embodiment, an additional moiety is conjugated to nucleotide bases of the probe such that, when the probe-target duplex is formed, the moieties are located within the major groove of the duplex.

Incorporation of a moiety in addition to the functional, chemical tail can serve to improve the probe hybridization properties. Examples of such moieties include minor groove binders and intercalators. Minor groove binders are described in U.S. Pat. Nos. 6,492,346 and 6,486,308, both of which are hereby incorporated herein by reference. In other embodiments, these moieties operate in conjunction with the functional tail R to aid in the detection of an endonuclease tail-cleavage reaction. Examples of such moieties include radioisotopes, radiolabelled molecules, fluorescent molecules or dyes, quenchers (dyes that quench fluorescence of other fluorescent dyes), fluorescent antibodies, enzymes, or chemiluminescent catalysts. Another suitable moiety is a ligand capable of binding to specific proteins which have been tagged with an enzyme, fluorescent molecule or other detectable molecule (for example, biotin, which binds to avidin or streptavidin, or a hemin molecule, which binds to the apoenzyme portion of catalase).

In a preferred embodiment, both the functional tail R and the additional moiety are dyes. One or both of the tail and additional moiety dyes can be fluorescent dyes. Preferably, one of the dyes is fluorescent. In one preferred embodiment the functional tail comprises a fluorescent dye and the additional moiety comprises a quencher. The fluorescent dye and quencher molecule operate together such that the fluorescence of the dye is repressed when the dye is bound to the AP site probe, but the fluorescence of the dye is detectable when the phosphodiester bond between the NA and tail R is hydrolyzed or cleaved by the enzyme. This fluorescence detection strategy is known as Fluorescence Resonance Energy Transfer (FRET). According to a FRET technique, one of the dyes servers as a reporter dye and the other dye is a quencher that substantially decreases or eliminates fluorescence of the reporter dye when both of the dyes are bound to the same molecule in proximity of each other. The fluorescence of the reporter dye is detected when released from the proximity of the quencher dye. Cleavage of the AP site probe functional tail releases the reporter dye from its quencher counterpart allowing for a detectable increase in the reporter fluorescence and detection of the target nucleic acids. The quenching dye can be a fluorescent dye or non-fluorescent dye (dark quencher). See, U.S. patent Publication Ser. No. 2003/0,113,765, U.S. Ser. No. 2003/0,096,254 and PCT Publication No. WO 01/42505 for fluorophore and quencher examples, both of which are hereby incorporated herein by reference.

The present invention includes a composition comprising a solid support and an AP site probe immobilized thereon. In such a case, one of the moieties conjugated to the probe can be a moiety that serves to attach the probe to the solid support. This moiety or solid support linker can be attached anywhere within or be a structural part of the NA and functional tail R structures of the probe of the present invention. In one embodiment, the AP site probe is covalently attached to a solid support through a Schiff base type linkage, as described in U.S. Pat. No. 6,548,652, incorporated herein by reference.

In assays of the present invention, a probe is typically included at concentrations of about 50-200 nM, more typically at concentrations of about 100-175 nM, and preferably at concentrations of about 150 nM. One of skill in the art will appreciate that the probe concentrations provided above can be altered depending on a variety of factors, including the amount of target, as well as the characteristics of the dye or quencher used.

C. Enhancer

An enhancer is an oligo- or polynucleotide designed to form a duplex with the target nucleic acid positioned immediately 5'- to the target-AP site probe. The combined, probe-enhancer-target complex simulates a naturally occurring nucleic acid atypical abasic site that is recognized by cellular exo- and endonuclease repair enzymes. Although the tail R cleavage reaction can be achieved without the enhancer, the presence of an enhancer generally improves the kinetics the reaction.

The structural requirements and limitations for an enhancer are essentially the same as for a NA component of an AP site probe, described above. Generally, the number of nucleotides in an enhancer oligonucleotide can range from 3 to 50, 100 or 200 nucleotides in length. Usually, the length of an enhancer is from 5 to 30 nucleotides. More typically, the length of the enhancer is 6-25, 7-20, or 8-15 nucleic acids. Most often, an enhancer component is about 10, 12, 14, 16, 18 or 20 nucleic acids in length. Usually, an enhancer oligonucleotide component will have a hybridization melting temperature of about 10 to 80° C., more typically of about 20 to 70° C., and preferably about 30° C., 40° C., 50° C., 60° C. or 70° C. An enhancer oligonucleotide will usually have a comparatively equal or higher hybridization melting temperature in comparison to the melting temperature of the NA component of the AP site probe. Usually, the melting temperature will be about 5 to 30° C., more typically about 10 to 20° C., and preferably about 8° C., 10° C., 15° C., or 20° C. higher than the melting temperature of the NA component of the AP site probe.

Preferably, the enhancer is DNA. An oligo- or polydeoxyribonucleotide enhancer is useful for detecting DNA and RNA target nucleic acids. The enhancer can also be RNA. In another embodiment, an enhancer can contain both DNA and RNA. Preferably, DNA bases are located at the 5'-end of the enhancer while RNA bases are at its 3'-end. Preferably, at least the four 5'-terminal bases of the enhancer are DNA bases.

In another embodiment, the enhancer contains nucleotides with modified, synthetic or unnatural bases, including any modification to the base, sugar or backbone. Preferably, modified bases increase thermal stability of the enhancer-target duplex in comparison to enhancer sequences that contain only natural bases. Specific modified bases are the same as those described for a probe.

In another embodiment, some or all nucleotides of the enhancer are substituted or contain independently different sugar-phosphate backbone modifications, including, 2'-O-alkyl RNA nucleotide, phosphorotioate internucleotide linkage, PNA (peptide nucleic acid), LNA (locked nucleic acid). References describing these and other potentially useful sugar-phosphate backbone modifications are provided above.

The enhancer optionally can contain some functional tails or markers conjugated to either end of the enhancer or in the middle of it. These moieties should not interfere with the template-specific cleavage of the probe R tail. In a preferred embodiment, these moieties are attached to the 3'-end of the enhancer. In another preferred embodiment, these moieties are conjugated to nucleotide bases of the enhancer such that, when the enhancer-target duplex is formed, the moieties are located within the major groove of this duplex. Enhancer moieties can serve to improve the enhancer hybridization properties. Examples of such moieties include minor groove binders and intercalators.

The present invention also encompasses a composition comprising an enhancer immobilized on a solid support. A moiety conjugated to the enhancer can serve to attach the enhancer to the solid support. This moiety or solid support linker can be attached anywhere within or be a structural part of the enhancer.

Modifications of the bases and sugar-phosphate backbone as well as other functional moieties conjugated to the enhancer can serve to improve the sequence specificity of target-enhancer duplex formation resulting in increased thermodynamic differences in binding between the enhancer and a matched target nucleic acid in comparison to binding between the enhancer and a mismatched target nucleic acid.

In assays of the present invention, an enhancer, when included, is typically added at concentrations of about 50-200 nM, more typically at concentrations of about 100-175 nM, and preferably at concentrations of about 150 nM.

D. Enzyme

An enzyme used in the present invention is an endonuclease or exonuclease that recognizes an Apurinic/Apyrimidinic (AP) site or atypical AP site moiety simulated by an AP site probe duplexed with a target nucleic acid complex, and preferentially hydrolyzes or cleaves the phosphodiester bond between the probe and the functional tail R. An enhancer can be used to increase the kinetics of the tail-cleavage reaction. An enzyme useful in the present methods preferentially does not cleave the NA part of the probe or the target nucleic acid. Otherwise, enzymes which cleave the probe NA or target nucleic acid at an efficiency that is substantially lower than target-specific tail cleavage can still find use in practicing the present methods. To minimize non-specific detection of the target nucleic acid, the enzyme preferentially does not cleave the tail R of the probe in absence of the target nucleic acid.

In a preferred embodiment, the enzyme is an AP endonuclease. The enzyme can be a class I or a class II AP endonuclease. Preferably, the enzyme is a class II endonuclease. Enzymes that belong to this family are isolated from variety of organisms, and any class II endonuclease that specifically recognizes an AP abasic site and specifically hydrolyzes the phosphodiester backbone on the 5' side of the AP site can be used in the present methods. Exemplified class II AP endonucleases include Endonuclease IV and Exonuclease III from *E. coli*, human APEI/REF-1 endonuclease, yeast APN1 endonuclease, exonuclease III homologous enzymes from *Drosophila* (Rrp1) and *Arabidopsis* (Arp) and thermostable endonuclease IV from *Thermotoga maritima*. Other AP endonucleases useful for detection and/or amplication systems requiring an AP site probe can be identified through the National Center for Biotechnological Information Entrez/PubMed nucleotide and protein databases accessed through the website www.ncbi.nlm.nih.gov/. Enzymes homogolous in structure and function to the *E. coli* Exonuclease III family of AP nucleases are also of use in the present invention (Mol, et al., *Mutat. Res.* 460:211 (2000); Ramotar, Biochem. *Cell Bio.* 75:327 (1997)). The structure and function of apurinic/apyrimidinic endonucleases is reviewed by Barzilay and Hickson in *Bioessays* 17:713 (1995).

In a preferred embodiment, the enzyme is an *E. coli* Endonuclease IV. An *E. coli* Endonuclease IV exhibits catalytic activity between room temperature (25° C.) and 75° C., preferably between 40-70° C. or 40-60° C., and more preferably between 60-70° C. or 65-75° C. The temperature of a target nucleic acid detection assay is preferably determined by the hybridization melting temperature of an AP site probe, where the temperature of the reaction conditions is preferably within 5, 4, 3, 2, 1 or 0 degrees, above or below, of the probe melting temperature, $T_m$. Optimum catalytic activity of an Endonuclease IV is observed within a pH range of 7.5-9.5, preferably between pH 8.0-9.0, most preferably at about pH 8.5-9.0. An abasic site assay using an Endonuclease IV enzyme is preferably carried out using a buffer that maintains a steady pH value of between 7.5-9.5 over varying temperatures. Preferred buffers include HEPPS (4-(2-hydroxyethyl)-1-piperazinpropan-sulfonic acid) and HEPES (4-(2-Hydroxyethyl)piperazine-1-ethanesulfonic acid). In a preferred embodiment, the buffer used is HEPPS-KOH. In certain embodiments, a TRIS buffer is also appropriate. Additional biological buffers of potential use can be found through Sigma-Aldrich (St. Louis, Mo., www.sigma-.com). Usually, the reaction conditions contain enzyme in nanomolar concentrations, but tail cleaving activity can be observed when the enzyme is provided in picomolar concentrations, and in certain cases in femtomolar concentrations.

E. Positioning of the Probe and Enhancer Binding Sites

Figure 2:
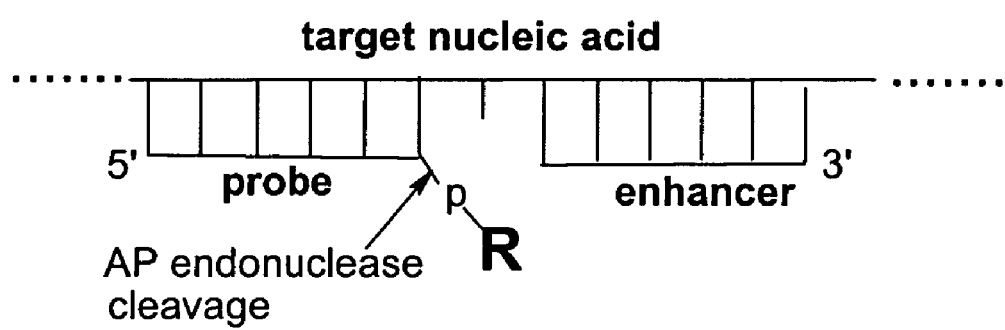
FIG. 2 illustrates a schematic diagram of the probe-enhancer-target nucleic acid complex that is recognized and cleaved by an AP endonuclease at the linkage shown by arrow. The presence of an enhancer-target duplex is not required for tail-cleavage. However, an enhancer-target duplex bound downstream from the probe usually improves the kinetics of the tail-cleavage reaction.

FIG. 2 shows an optimal design of the probe and enhancer to achieve the highest yield of the tail-cleavage reaction. The probe and enhancer form duplexes with the target nucleic acid that are positioned next to each other leaving one, non-paired base of the target between the duplexes. This design simulates the naturally occurring lesion 2 that is shown in FIG. 1. Although this is a preferred design, cleavage of the tail R in the target-probe complex can be achieved in absence of the enhancer, or when the number of non-paired, target polynucleotide bases between two duplexes shown is 0, 2 or more bases. All these designs are within the scope of the present invention.

Including an enhancer can be desirable, especially when using an enzyme of the *E. coli* Endonuclease IV family, because the enzyme tail-cleavage rate, as measured by detectable reporter signal, can be increased 6, 7, 8, 9, or 10 fold in comparison to the tail-cleavage rates in the absence of an enhancer.

F. Cycling of the Tail Cleavage Reaction

In the past, probes used in cycling probe assays have typically positioned a cleavable linker somewhere within the middle of a probe sequence. This design is believed to provide a strong thermodynamic factor to drive the cycling process when the target polynucleotide is recycled during the reaction. Cleavage of the probe within the middle of the nucleotide sequence leads to products that are shorter in length and that have weaker hybridization properties than the intact probe. At optimal reaction conditions that are typically below the probe $T_m$, the product-target complexes fall apart, quickly recycling the target nucleic acid for binding with other intact probe molecules.

Figure 17:
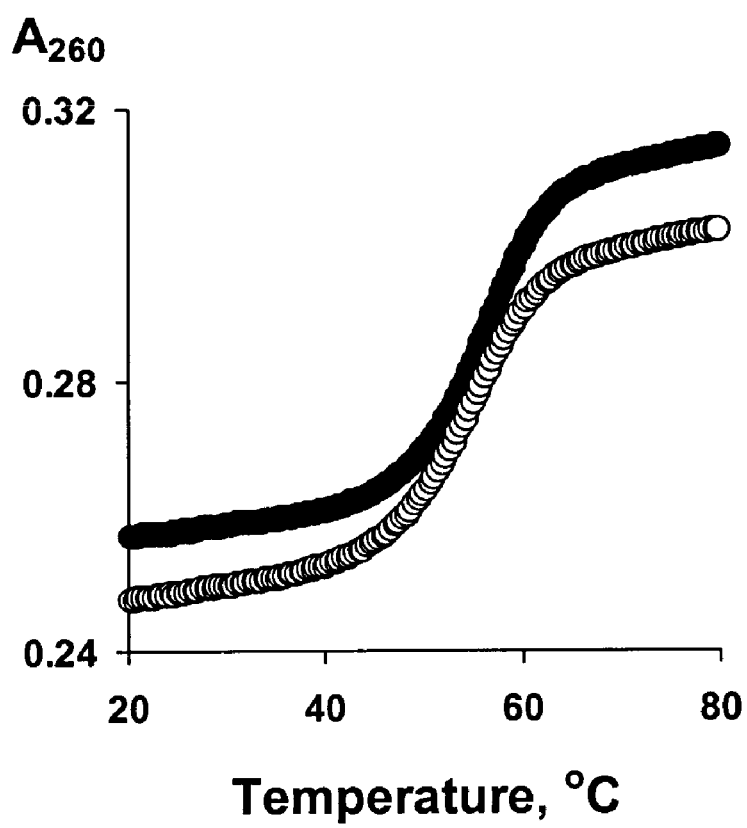
FIG. 17 illustrates that cleavage of a fluorescent functional tail R from an AP site probe does not effect on the probe hybridization properties. Melting curves of the intact and cleaved probes are shown by white and black dots respectively. The assay is described in Example 6, infra.

The probe design in the present invention lacks a thermodynamic, cycling-driven factor. The hybridization properties of the probe remain essentially the same before and after the tail cleavage reaction. See FIG. 17. An AP site probe having a cleavable functional tail at the 3' end of the probe also supports a cycling mechanism. The target nucleic acid remains intact after tail cleavage and is available to bind another AP site probe having a cleavable functional tail. Typically, the number of the cleaved probes per target molecules is greater than one, more typically about 5, 10, 20, or 30, and can be as many as 40 or 50. Without being bound to any particular theory, the cycling observed herein appears to be "kinetically driven" in contrast to "thermodynamically driven" cycling disclosed by others and it is conceivably the result of several factors. First, when the reaction temperature is close to the probe hybridization melting temperature such that the lifetime of the probe-target complex is relatively short, it leads to a rapid exchange of the probe molecules in the probe-target duplex. As a general rule, the closer the reaction temperature is to the probe $T_m$, the faster the cycling. Second, when the tail-ON probe concentration is in excess over the tail-OFF product, for instance, at the earlier stages of the reaction, the tail-ON probe is predominantly supplied to the reaction complex, facilitating cycling. It is understood, within the scope of present invention, that an optimal reaction temperature of the AP site probe cleaving assay, a temperature at which the observed cleavage rate is maximum, can be different from the melting temperature of the AP-site probe. It can be lower or higher than the AP probe $T_m$. This is due to factors effecting the AP site probe cleavage reaction. Examples of these factors are AP endonuclease activity at different temperatures, elements of secondary structures within the nucleic acid components of the reaction, target nucleic acid, AP site probe and enhancer that compete with the formation of the desired active complex (see FIG. 2). Finally, the Endonuclease can preferentially bind to and stabilize the tail-ON probe-target nucleic acid duplex over the tail-OFF complex, promoting the cycling process.

G. Detection of the Endonuclease Tail-Cleavage Reaction

Either part of the endonuclease tail-cleavage reaction, the NA containing part or the tail R containing part or alternatively both of them independently, can be detected. Suitable reporter groups for attaching to the functional tail R include beads, nanoparticles (Taton, et al., *Science* 289:1757 (2000), chemiluminescers, isotopes, enzymes and fluorophores. A variety of physical or chemical methods can be used for detection of the cleavage product. Depending on the nature of the markers used, these methods include, for example, chromatography and electron-, UV-, IR-, mass-, radio-, fluorescence spectroscopy including fluorescence polarization and the like.

Figure 7:
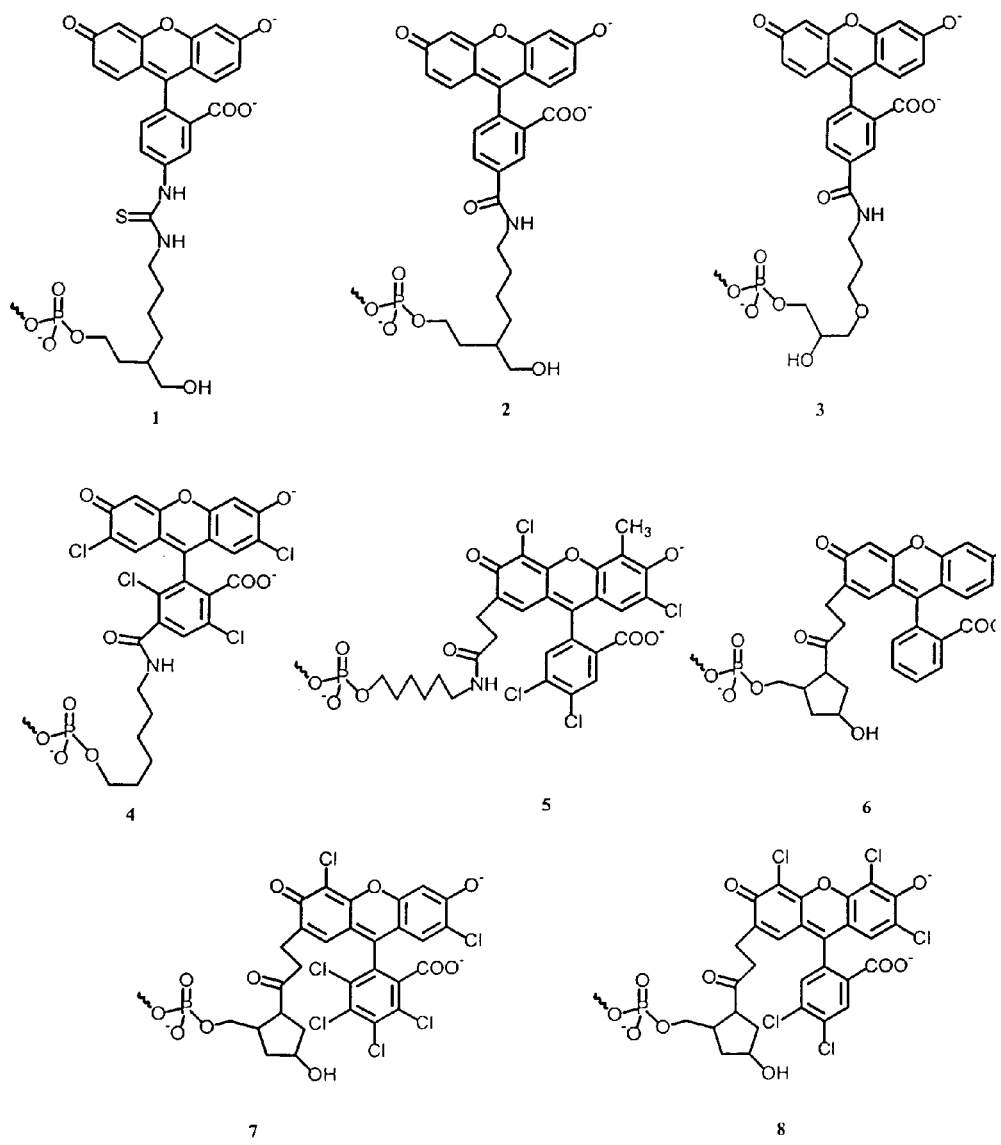
FIG. 7 illustrates exemplified fluorescein flurophores and linkers that can be incorporated in the functional tail R

In a preferred embodiment, cleavage of the functional tail R comprises a fluorophore reporter group and is detected by fluorescence spectroscopy. Suitable fluorophores include the resorufin dyes, coumarin dyes, xanthene dyes, cyanine dyes, BODIPY dyes and pyrenes. Preferably, the functional tail R comprises a fluorescent dye with a xanthene core structure. Exemplified dyes with a xanthene core structure are depicted in FIG. 7. Additional fluorophores appropriate for incorporation into the functional tail R are described in PCT Publication No. WO 01/142505 and in Haugland, *Handbook of Fluorescent Probes and Research Products*, Ninth Ed., (2002), published by Molecular Probes, Eugene, Oreg. (accessible at www.probes.com/handbook/).

In some embodiments, background fluorescence of a fluorophore incorporated on the functional tail R, is minimized by attaching a quencher to the AP site probe. Typically, a quenching molecule is covalently attached to the 5' end of the probe through a linker that is not cleaved by an enzyme. In some embodiments, a quencher is linked to the middle or the 3' end of the probe. When a quencher is attached to the 3' end of the probe, it is usually incorporated into the functional tail R as a "cleavable quencher," and the fluorophore is then attached to the middle or the 5' end of the probe. In preferred embodiments the quencher comprises a dye core structure shown in FIG. 8. However, any molecule that neutralizes or masks the fluorescence of a fluorophore incorporated in an uncleaved functional tail R finds use as a quencher in the present invention. Other quencher molecules suitable to attach to an AP site probe and guidance for selecting appropriate quencher and fluorophore pairs is provided in Haugland, supra. Additional guidance is provided in U.S. Pat. Nos. 3,996,345 and 4,351,760, and U.S. Publication Ser. Nos. 2003/0096,254 and 2003/0113,765 and in co-owned U.S. patent application Ser. No. 09/457,616, filed on Dec. 8, 1999, each of which is hereby incorporated herein by reference.

Figure 8:
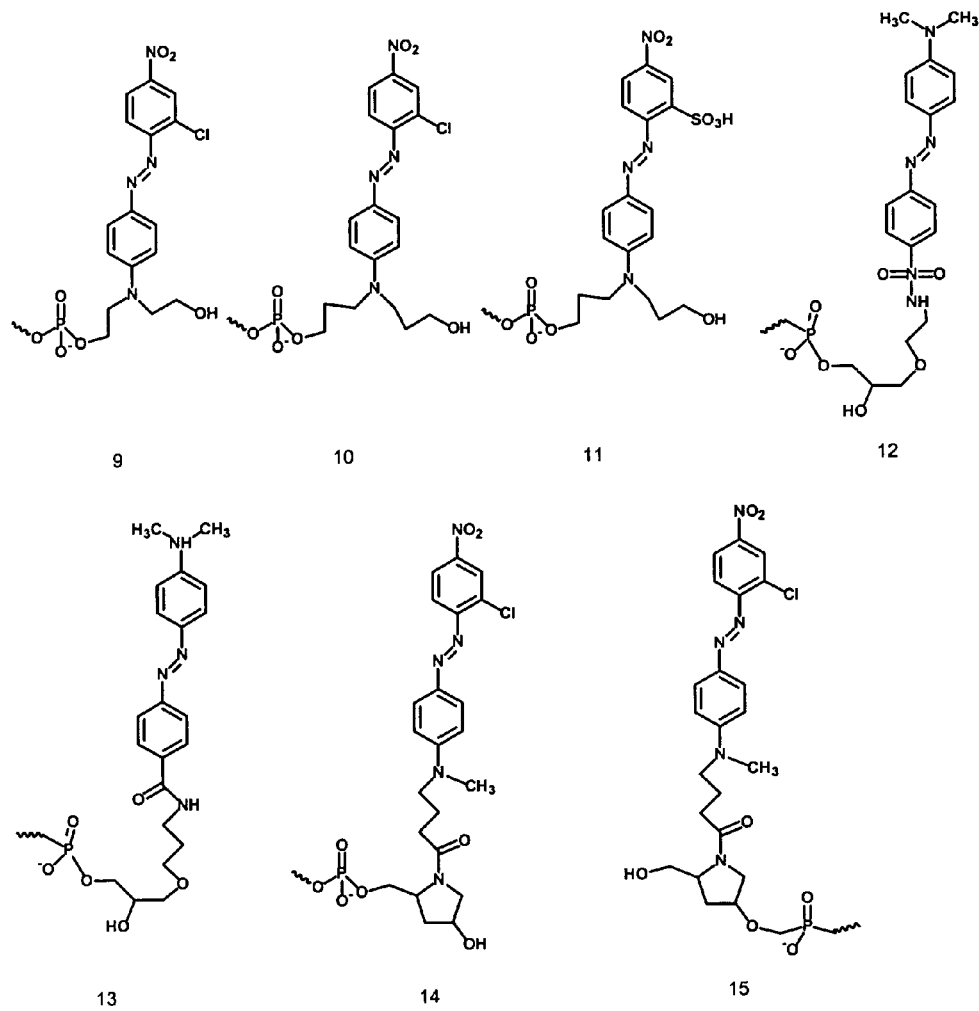
FIG. 8 illustrates exemplified cleavable quenchers and linkers that can be incorporated in the functional tail R. Quencher molecules without cleavable linkers can be incorporated in the middle or at the 5' end of an AP site probe. Structure 15 is an example of incorporation of a preferred quencher to the 5'-end of AP site probe.

Fluorophore and cleavable quencher molecules are typically attached to an AP site probe through a linker that is specifically cleaved by an enzyme. A linker can be rigid or flexible. Preferably the linker structurally mimics a naturally occurring abasic site (see, FIG. 9), and is cleaved by an Endonuclease IV. Preferably the C1 carbon of the linker, attached to the phosphate, is a primary carbon. Preferably the linker comprises a phosphate. Exemplified linkers for attaching a fluorophore or cleavable quencher molecule to a AP site probe are depicted in FIGS. 7 and 8. Suitable commercially available chemical linkers can be purchased through Pierce Biotechnology, Rockford, Ill. and Molecular Probes, Eugene, Oreg. Suitable methods for attaching reporter groups such as fluorophores and quenchers through linkers to oligonucleotides are described in, for example, U.S. Pat. Nos. 5,512,677; 5,419,966; 5,696,251; 5,585,481; 5,942,610 and 5,736,626, each of which are hereby incorporated herein by reference.

Figure 9:
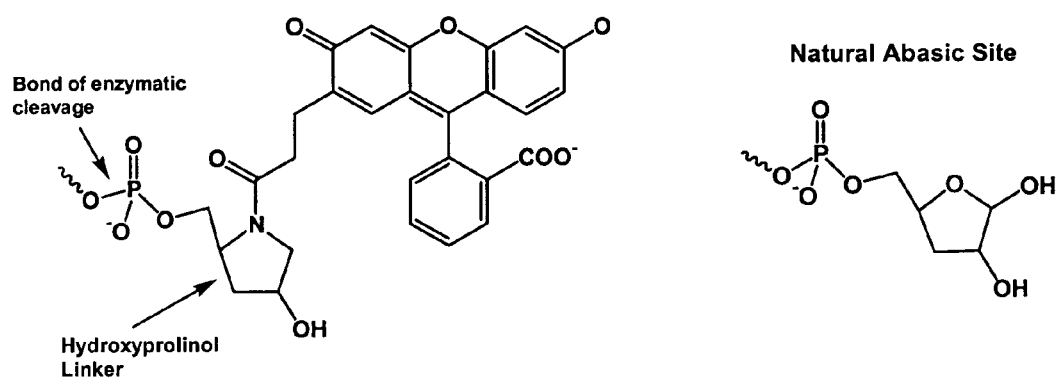
FIG. 9 illustrates the preferred hydroxyprolinol linker and compares its structure to a natural abasic site.

In a preferred embodiment the linker is a rigid linker. In one preferred embodiment, the rigid linker is a hydroxyprolinol linker, such as is depicted in FIG. 9. Hydroxyprolinol linkages are described in U.S. Pat. Nos. 5,419,966; 5,512,677; 5,519,134; and 5,574,142 each of which is incorporated herein by reference. Cleavage of the functional tail R attached through a rigid linker, i.e., a hydroxyprolinol linker, requires greater concentrations of enzyme and exhibits decreased catalytic rates, but is highly specific. Generally, the Endonuclease IV enzyme does not detectably cleave functional tails R attached to an AP site probe through a rigid linker, such as a hydroxyprolinol linker, in the absence of a target nucleic acid.

In some embodiments, it is desirable to attach the functional tail R through a flexible linker. Cleavage of the functional tail R is more efficient when attached through a flexible linker, however, decreased specificity is observed because detectable tail-cleavage occurs in the absence of a target nucleic acid. Non-specific cleavage of functional tails R attached through a flexible linker can be minimized by adding a competitive binding substrate that is more favorable to the enzyme than an unduplexed probe but less favorable than the probe duplexed with a target nucleic acid, i.e., a "decoy." In one embodiment unmelted genomic DNA is added to the reaction as a decoy to minimize cleavage of the AP site probe functional tail R in the absence of a target nucleic acid.

Figure 10:
FIG. 10 illustrates a hairpin structure (SEQ ID NO:1) simulating a probe-target nucleic acid-enhancer complex as a model substrate for an AP endonuclease. Cleavage of this substrate in reaction with E. coli endonuclease IV is also shown on FIG. 10. The reaction was monitored as fluorescence vs. time in 5 mM $MgCl_2$, 20 mM Tris-HCl (pH8.5). Experiment was performed on ABI PRISM™ 7700 Sequence Detector at 60° C. with the hairpin substrate concentration of 150 nM and the enzyme concentration of 0.0004 U/µL. Structure of the tail used in this example is shown in FIG. 7, structure #2.
Figure 10:
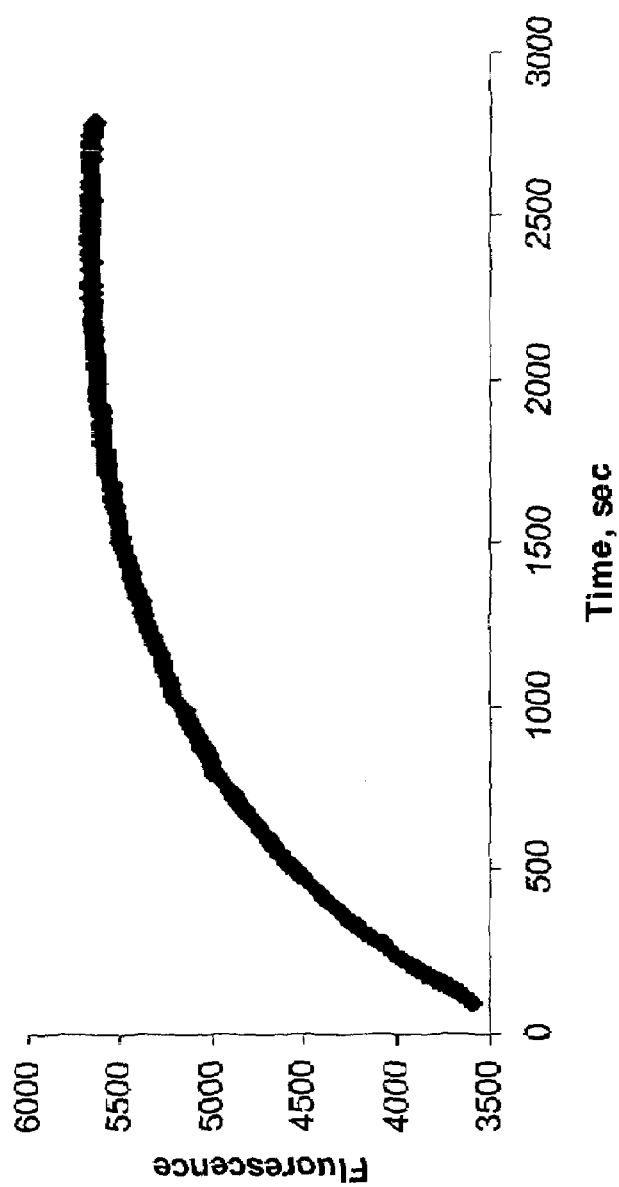

The ability of particular tail structures to serve as specific substrates of an AP endonuclease can be determined using an assay that provides a probe/target nucleic acid/enhancer complex as a single hairpin structure, exemplified in FIG. 10. Preferably the hairpin structure has one unpaired nucleic acid, thereby simulating a naturally occurring abasic site residing in duplexed nucleic acids. In other embodiments, the test assay hairpin structure can have zero or two unpaired nucleic acids. In such a test assay, the cleavage of the functional tail R is detected by measuring the release of the reporter group attached to a hairpin structure in comparison to release of the reporter group attached to an unduplexed AP site probe. A tail structure that serves as a specific substrate for an AP endonuclease will be cleaved from a hairpin structure at a faster catalytic rate in comparison to its cleavage rate from an unduplexed AP site probe. A tail structure that serves as a specific substrate preferably exhibits a ratio of specific cleavage, in the presence of the hairpin structure, to non-specific cleavage, in the presence of an unduplexed AP site probe, of at least 50-, 75-, or 100-fold, more preferably of 300-, 400-, 500-, 600-, 700-, 800-, 900- or 1000-fold, and can exhibit ratios of greater than 1000-fold, as measured by the reporter group signal (i.e., Fluorescence Units per minute of a fluorphore reporter group). The hairpin substrate design exemplified on FIG. 10A does not incorporate a quencher moiety. Nevertheless AP endonuclease cleavage of the fluorescent tail increases the dye fluorescence by approximately two times (FIG. 10B). The fluorescent signal outcome of the assay can be improved by incorporation of a quenching moiety within the hairpin sequence that represents an enhancer. Those skilled in the art will appreciate that the hairpin substrate exemplified in FIG. 10 can be used for detection as well as for quantitative measurement of AP endonuclease activity in different media.

In other embodiments, the NA part of the AP site probe is detected. For instance, the products of the probe tail-cleavage reaction can be detected as a result of another reaction that follows the cleavage reaction or occurs simultaneously with it. Cleavage of the tail R from the probe generates a "free" 3'-hydroxyl group that can be, for example, extended by a polymerase in a template-dependent polynucleotide synthesis in the presence of NTPs such that the tail-OFF probe would serve as a primer complexed with template. In some embodiments, the strands of a probe extension nucleotide synthesis are the detectable reaction product. Some NTPs incorporated in a probe extension can optionally carry a detectable marker. Incorporation of one or more detectable markers into a probe extension product simplifies the detection of the synthesized nucleotide strands.

Figure 3:
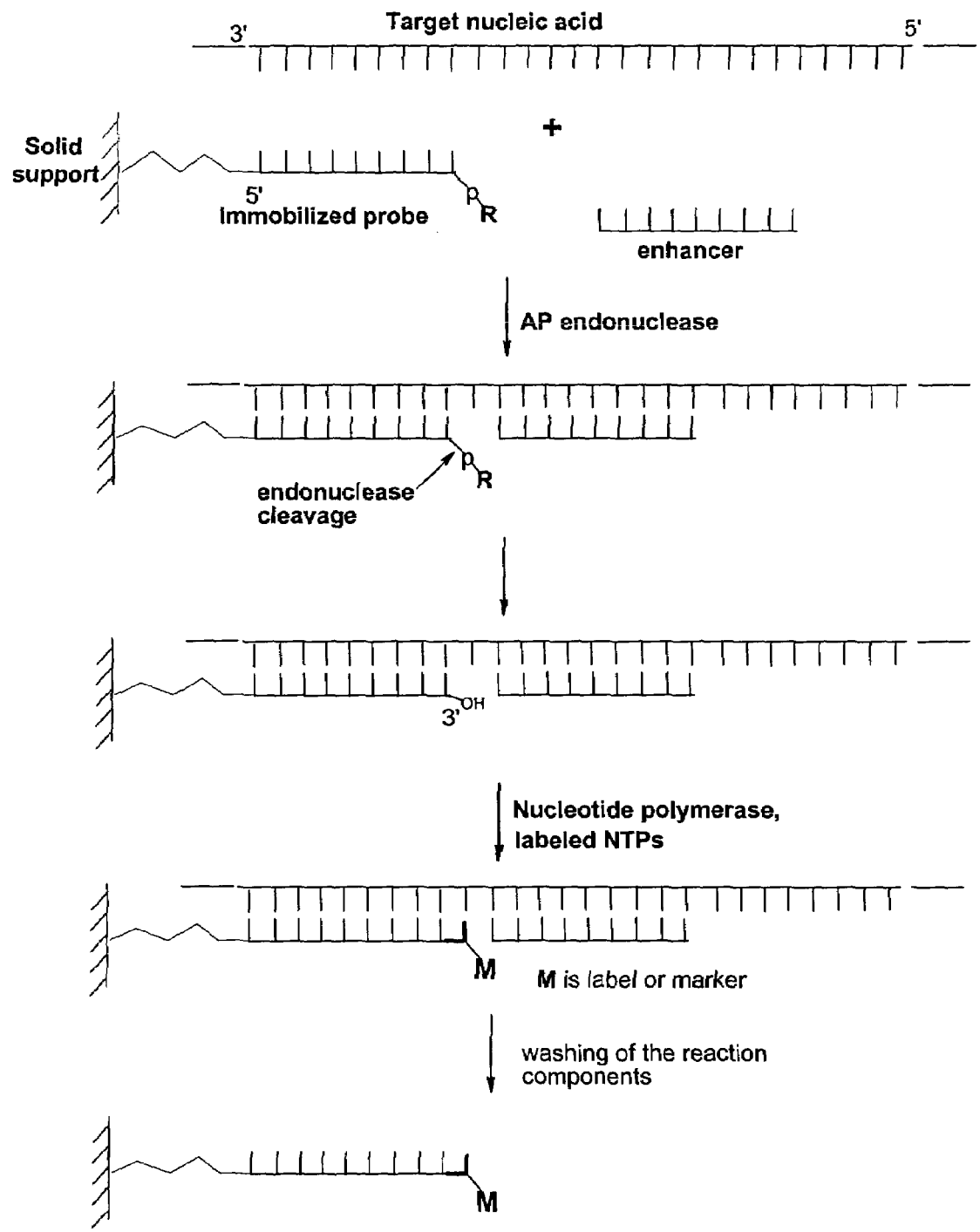
FIG. 3 illustrates a schematic diagram of a solid support base assay that incorporates both tail cleavage and probe extension reactions for target nucleic acid detection. Probe having a cleavable tail is immobilized on a solid support. The target nucleic acid, enhancer and probe comprise a substrate complex that facilitates endonuclease cleavage of the -p-R tail, resulting in a 3'-OH group on the probe that can be extended by a nucleotide polymerase. Nucleotide 5'-triphosphates (NTPs) are labeled with a specific label or marker. In the example shown, polymerization is terminated after incorporation of a labeled nucleotide. After the removal of the excess labeled NTPs by washing, the labeled probe is bound to the solid support and presence of the target nucleic acid duplexed with the probe can be detected. In addition to the target nucleotide detection, this approach allows the determination of the sequence of the target nucleotide that is 3' from the duplexed region. In such cases, every NTP needs to be labeled by a specific marker. "R" represents a functional chemical tail.

The excess unincorporated NTPs carrying a detectable marker need to be removed from the reaction mixture in order to detect the synthesized strands of the probe extension. This can be achieved when the reaction complex shown on FIG. 2 is immobilized on a solid support. The complex can be immobilized before or after the combined tail cleavage/probe extension reaction is completed. A schematic diagram of such an assay is shown on FIG. 3.

Figure 4:
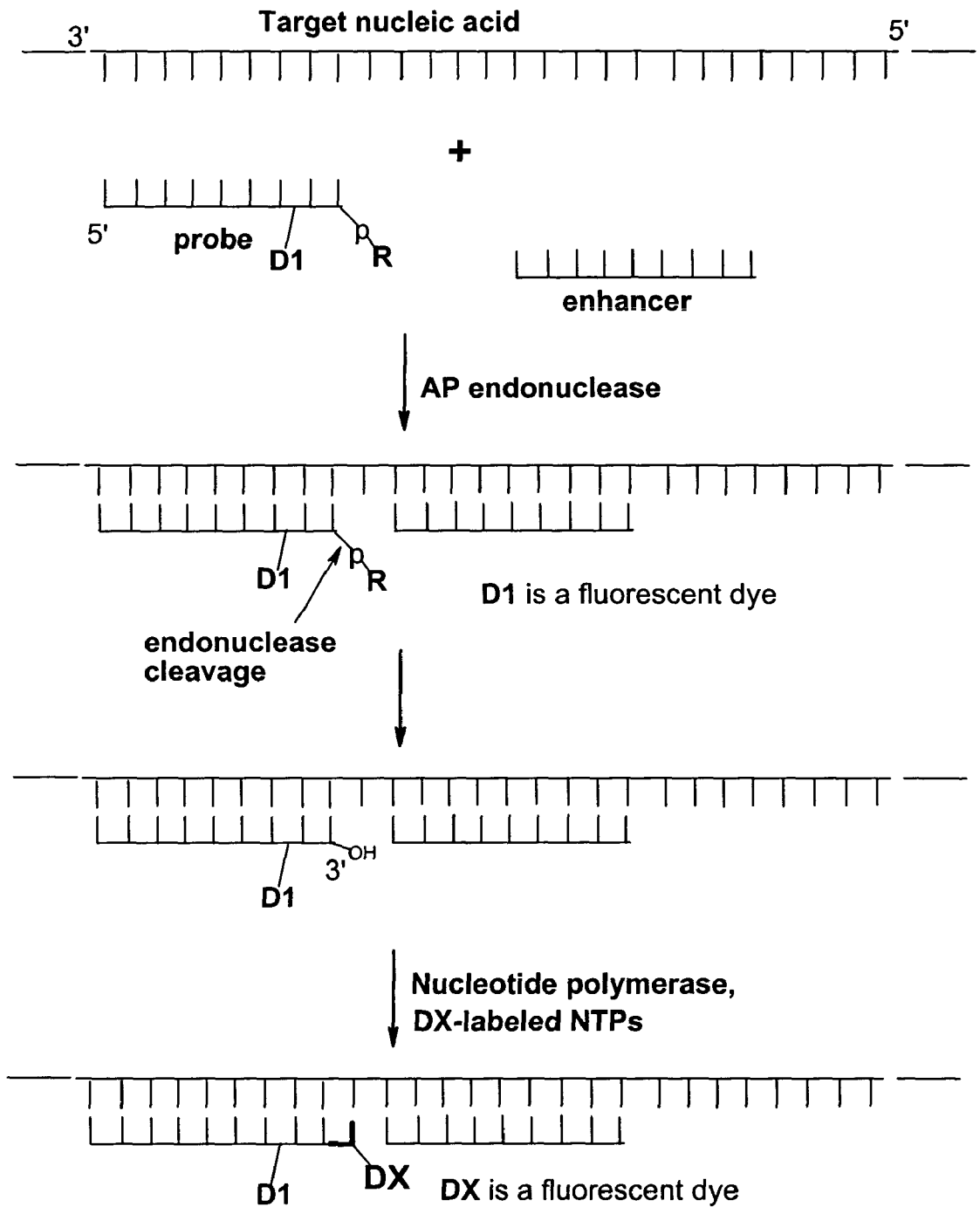
FIG. 4 illustrates a schematic diagram of an assay that incorporates both the tail cleavage and probe extension reactions for target nucleic acid detection. "D1" is a fluorescent dye and "DX" is a fluorescent dye other than D1. Both dyes are selected to support a Fluorescence Resonance Energy Transfer ("FRET") effect so emission of D1 overlaps with the absorbance of the DX. FRET is used to distinguish two or more dyes within the same molecule or complex from two or more dyes attached to different molecules. The reaction mixture is irradiated at a wavelength that is within the absorbance of D1 but not DX; fluorescence of the reaction mixture is measured within the range of emission of the DX dye. DX dye is detected in the mixture only when this moiety is incorporated into the probe sequence. DX could be one or more dyes. For example, every NTP can be labeled with a particular dye. For an optimal FRET effect, D1 is preferentially conjugated close to the 3' end of the probe. The conjugation must not block either the tail-cleavage site or the probe extension reactions.

Although immobilization is an effective way to remove the excess of the labeled NTPs, labeled NTPs can also be removed in solution phase. An example of such an approach is shown on FIG. 4. Of course, inclusion of an enhancer is optional in AP site probe extension or amplification assays.

H. Solid Support Tail Cleaving Assay

The target nucleic acid-probe-enhancer complex can be covalently attached to a solid support via a linker or linkers coupled to one, or independently to two, components of the probe-target-enhancer complex. Immobilization of the complex also can be achieved through non-covalent binding, including affinity, charge or hydrophobic interaction. Immobilization can be performed before or after the tail cleaving reaction. The solid support material can be, for example, latex, plastic, derivatized plastic, polystyrene, magnetic or non-magnetic metal, glass or silicon surface or surfaces of test tubes, microtiter wells, sheets, beads, microparticles, chips, and other configurations known to those of ordinary skill in the art. Such materials can be used in suitable shapes, such as films, sheets and plates, or they can be coated onto or bonded or laminated to appropriate inert carriers, such as paper, glass, plastic films, or fabrics.

I. Probe and Enhancer Bound Together Through a Linker

Figure 5:
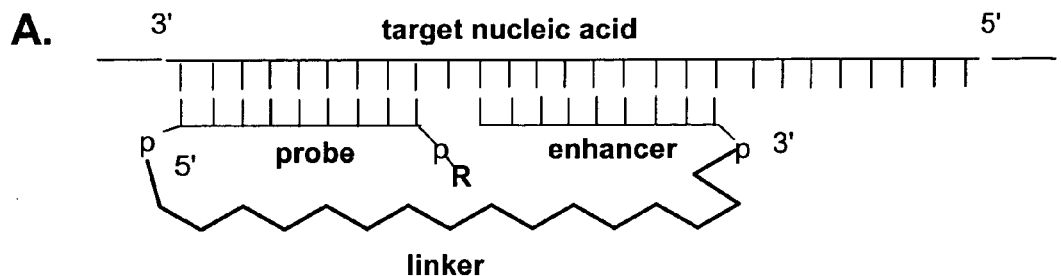
FIG. 5 illustrates a schematic of exemplified linkage strategies to link 5'-end of a probe and 3'-end of an enhancer either covalently (A) or non-covalently (B).
Figure 5:
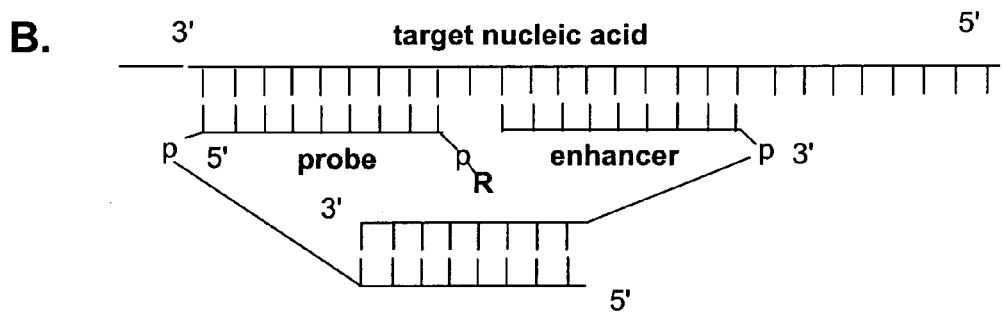

In one embodiment, a probe is linked to an enhancer so as these two components of the reaction complex are associated with each other during the tail cleaving reaction. The linker can be a covalent or a non-covalent linker, i.e., when interaction between a probe and enhancer is provided by hydrogen bonds or Van der Waals forces. A probe-enhancer linker can be attached at any position within the probe and enhancer. Preferably, the linker does not block the tail cleaving reaction, and is of an appropriate length to support the tail cleaving reaction. Further, a linker useful in a tail cleaving assay will not compromise the ability of the AP site probe or enhancer to form duplexes with a target nucleic acid. Finally, a preferred linker is not cleaved by an AP endonuclease. FIG. 5 schematically depicts two possible arrangements of linkers between a probe and an enhancer. When attached through a linker, the probe and enhancer are components of one molecule or complex. Linked probe-enhancer molecules or complexes can be immobilized on a solid support.

In preferred embodiments, a probe-enhancer linker is comprised of individual or combined repeats of substituted alkyl backbone moieties, including $(-OCH_2CH_2-)_n$, $(-OCH_2CH_2-OPO_2-)_n$ or $-O(CH_2)_nO-$. Typically, n is from 1-100, more typically n is 10, 20, 40, 50, 60 or 80. In other embodiments, a linker is a flexible polypeptide chain, for instance, dihydropyrroloindole peptides or a series of one or more repeats of a Gly-(Ser)$_4$ (SEQ ID NO:2) polypeptide sequence. In another embodiment, the linker is an oligonucleotide, such as poly A or poly T and the like. In yet another embodiment, the linker is an alkyl chain having a backbone typically of about 100, 200 or 300 atoms, more typically of about 40, 60 or 80 atoms. Other alkyl linkers of potential use are described in U.S. Patent Publication No. 2003/0113765, incorporated herein by reference. Additional linkers that may find use are described by Dempey, et al., *Nucleic Acids Res.* 27:2931 (1999); Lukhtanov, et al., *Nucleic Acids Res.* 25:5077 (1997); Lukhtanov, et al., *Bioconjug. Chem.* 7:564 (1996); and Lukhtanov, et al., *Bioconjug. Chem.* 6:418 (1995). Appropriate linkers can be obtained from commercially available sources, for example from Pierce Biotechnology, Rockford Ill. (www.piercenet.com/). Guidance for selecting an appropriate linker for attaching oligonucleotides is provided in Haugland, *Handbook of Fluorescent Probes and Research Products*, supra. These linkers also find application in attaching an AP site probe or an enhancer to a solid support.

IV. Applications of AP Endonuclease Tail-Cleavage Systems

A. Amplification of Nucleic Acids Using Primer Cleaving Technology

An AP site probe can also function as a primer and its use in detection of nucleic acid sequences can be combined with amplification techniques in several ways. Amplification can be carried out before or simultaneously with cleaving the functional tail R from an AP site probe.

In one approach, the target nucleic acids are first amplified, and then with or without additional isolation or purification from the amplification mixture sample, contacted with an AP site probe, an enhancer and an AP endonuclease.

In another approach, the target amplification and target detection are simultaneously run in the same reaction mixture. This approach allows the detection of a target nucleic acid in real time by detecting tail-cleavage products during the amplification reaction. In some embodiments, a fluorescent signal generated by cleavage of a tail with a fluorescent dye is visually detected. Simultaneous amplification and detection also allows measurement of an amount of target nucleic acids in the test sample. When the target amplification and detection are run simultaneously, reaction conditions (i.e., salt composition and reaction component concentrations, pH, and temperature of the reaction) are designed such that they support both amplification and detection. Also, the detection and amplification processes must not interfere with each other such that the combined assay is disabled. For example, if PCR is used to amplify the target DNA, the AP endonuclease used should be catalytically active at elevated temperatures (typically 80-100° C.) used in PCR to melt double stranded DNA during the amplification cycles. This can be achieved by use of thermostable AP endonuclease (see, PCT Publication No. WO 93/20191, herein incorporated by reference), addition to the reaction buffer some special component that increase thermostability of the enzyme, for example, trehalose (see, Carninci, P., et al., Thermostabilization and thermoactivation of thermolabile enzymes by trehalose and its application for the synthesis of full length cDNA (1998) *Proc. Natl. Acad. Sci. USA*, 95, 520-524), or a combination of both these approaches.

By contrast, isothermal amplification techniques generally do not require temperature changes during the target amplification and can be carried out over a wide range of temperatures, i.e., from 20° C. to 70° C. The selected temperature will depend on the thermal stability of the enzymes used and optimal assay conditions. Isothermal amplification assays can be combined with known AP endonucleases. Examples of such AP endonucleases include without limitation Endonuclease IV from *E. coli* that is stable up to 70° C., human APE endonuclease, and yeast AP endonuclease.

Figure 6:
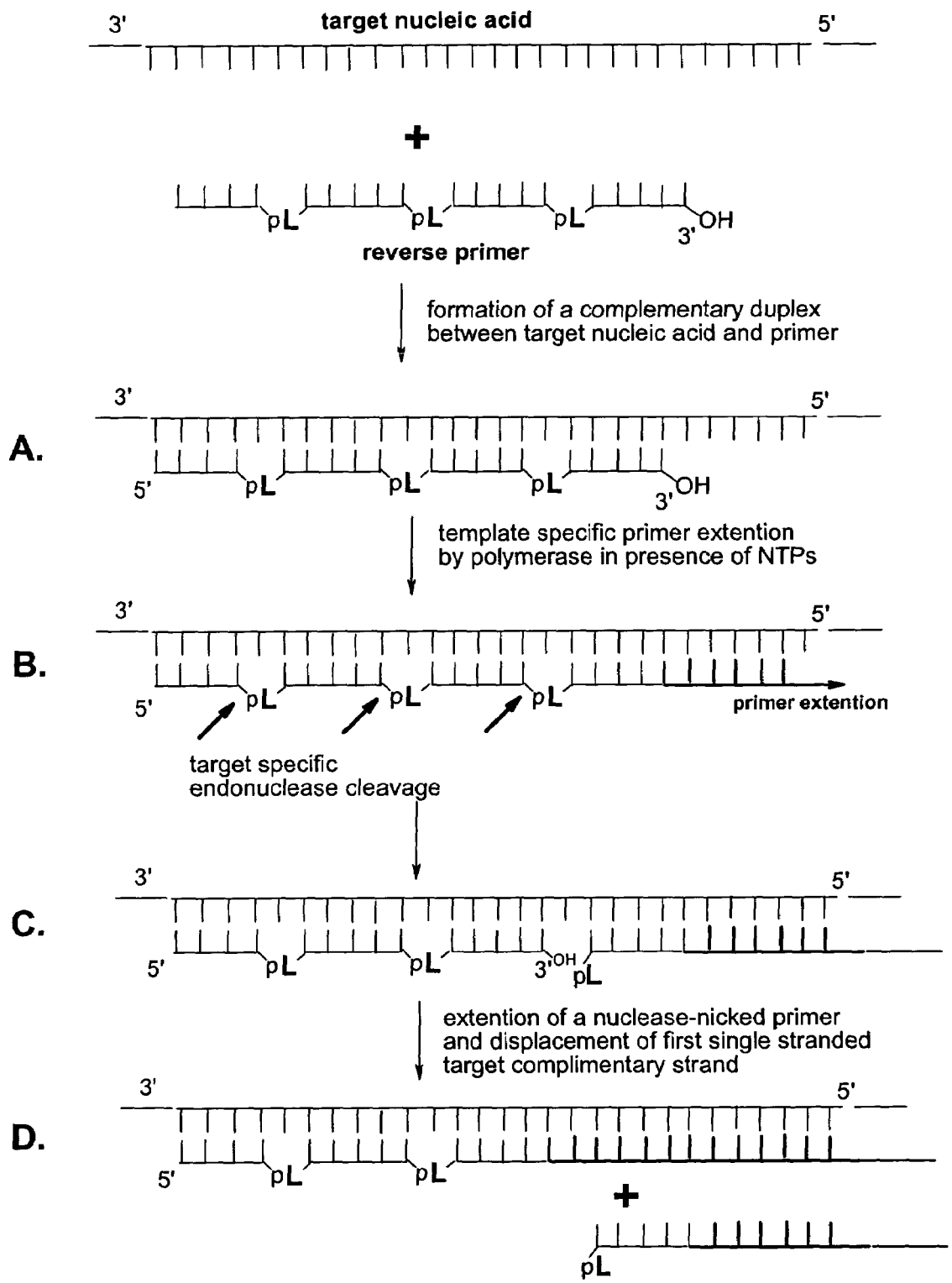
FIG. 6 illustrates a schematic diagram that shows the initial stages of a target nucleic acid amplification by a method of the present invention. At stage A, a primer that has multiple, endonuclease cleavable linker sites ("pL") incorporated randomly through its sequence binds to the target nucleic acid strand. At stage B, polymerase extension originates from a 3' end of a primer to provide a duplex. At stage C, an endonuclease cleaves the pL linker sites, providing available 3'-hydroxy groups for polymerase extension. At stage D, a subsequent extension reaction originating from an cleavable linker site displaces a previously synthesized strand. This method allows multiple copies of a complementary target nucleic acid strand to be synthesized from one target nucleic acid strand.

As illustrated in FIG. 6, the invention further provides for amplification of a target sequence using primers with internal AP endonuclease cleavage sites having a sequence structure $(NA_1-L)_m-NA_2$, where $NA_1$ and $NA_2$ are nucleic acid sequences complementary to the target nucleic acid, L is an endonuclease-cleavable linker and m is from 0 to 100. Primers having internal AP endonuclease cleavage sites hybridized to a target nucleic acid can function as primers for a polymerase extension once a 3' functional tail or an internal linker cleavage site (pL) simulating an abasic site is cleaved, leaving an available 3'-OH group. In a primer that contains several pL sites, an AP endonuclease cleaves pL sites, thereby generating 3'-OH priming sites for the polymerase. The polymerase synthesizes a complementary nucleic acid sequence extending from the newly formed primer that displaces a previously synthesized complementary nucleic acid strand from a downstream pL cleavage site. Each synthesized strand serves as a template for a forward primer. With this amplification scheme, the number of target nucleic acid copies that can be generated from one primer is equal to the number of pL linker cleavage sites. To facilitate exponential amplification of a desired amplicon, at least one of the primers should have more than one pL linker while the other primer has at least one pL linker. Greater numbers of pL linkers within the primer sequences will result in more efficient amplification of a desired target sequences.

For amplification of a nucleic acid sequence of interest from an AP site primer, it is preferable that polymerase activity in the reaction mixture dominates over endonuclease activity. This could be achieved, for example, by balancing of the relative enzyme concentrations (polymerase vs. endonuclease). Preferably, the endonuclease cleaves pL linkers only when a primer or product of its extension is duplexed with a target nucleic acid strand. Further, the polymerase used for amplification using an AP site primer preferably lacks the 5'-3' exo or endonuclease activity and 3'-5' exonuclease activity (proof reading). Finally, the polymerase used in an AP site primer amplification scheme preferably "reads through" or extends over templates that have incorporated pL linker sites. It is also preferred that the polymerase incorporates any natural base against the pL linker during chain elongation. Under appropriate reaction conditions, the activities of the polymerase and the endonuclease should allow for isothermal amplification of both strands of a desired amplicon within a nucleic acid target sequence located between and including the sequences of a forward and a reverse primer. Nucleic acid amplification using AP site primers can be combined with nucleic acid detection resulting from functional cleavage because AP site cleavage in either instance is catalyzed by the same endonuclease.

B. Detection of Nucleic Acid Polymorphism Using AP Site Tail Cleaving Technology AP site probes are particularly suited for DNA genotyping or detection of two related target nucleic acids that share essentially the same sequence and that are different by a number of bases within the sequence of interest. Most commonly, the difference in the target DNA sequences of interest are as small as one base (SNP). AP endonucleases generally bind to the DNA on either side from an abasic site and are affected by mismatched base pairs residing in proximity to their preferred enzyme binding site. A mismatched base pair that resides within the region of an AP endonuclease binding site has a negative effect on the enzyme-DNA-substrate binding, and consequently impedes the catalytic rate of tail-cleavage, as measured by a detectable reporter group signal. AP endonucleases identify mismatched base pairs located in the region of their binding sites by preferentially cleaving the functional tails R of an AP site probe duplexed with a target nucleic acid sequence having matched base pairs located outside the enzyme binding region in comparison to cleaving the tail R of a probe duplexed with a target nucleic acid having mismatched base pairs in the enzyme binding region.

AP site probes find particular use in detecting base pair mismatches that potentially exist at a known or suspected location in a target nucleic acid. Usually in such assays, two or more different AP site probes are contacted with one or more target nucleic acids in a sample, each probe having a nucleic acid sequence differing at one or more bases and distinctly detectable reporter groups. For instance, the two or more AP site probes could each have a functional tail comprising a fluorophore with detectably distinct emission wavelengths, for instance 6-fluorescein or Green Dye (FIG. 7, structure 6) and Yakima Yellow (FIG. 7, structure 5). When Endonuclease IV from $E.$ $coli$ is used in the assay, discriminatory cleavage of a functional tail R is most pronounced when the base pair mismatches are located at the 3' end of an AP site probe in a probe-target nucleic acid duplex. Preferably, the mismatch is positioned within 8 nucleotides from the 3' end of the probe, more preferably at the 7, 6, 5, 4 or 3 position from the 3' end of the probe, and most preferably at the 1 or 2 position from the 3' end of the probe, where position 1 is the 3' end nucleotide. In a most preferred embodiment the mismatch is located at position 2 from the 3' end of the probe. Base pair mismatch identification assays using an AP site probe can be conveniently carried out in combination with amplification systems, particularly with isothermal amplification systems.

An AP site probe used in base pair mismatch identification generally is about 6-18 nucleotides in length, more preferably about 6-16 nucleotides in length. If the probe is comprised entirely of naturally occurring base pairs, it is preferably about 10-16 nucleotides. AP site probes from a universal probe library also find use in tail cleavage base pair mismatch identification assays. Universal library oligonucleotides of 5, 6, 7 or 8 nucleotides can be used, particularly those which are comprised at least in part of modified bases.

C. AP Site Probes Constructed from a Universal Library

The present invention contemplates AP site probes constructed from a universal library. By "universal library" is intended all possible permutations of the naturally occurring nucleotide bases for a particular nucleotide length. Generally, a universal library for an oligonucleotide of n nucleotides is $4^n$ members. For example, the universal library for an oligonucleotide of 6 nucleotides in length is $4^6$ or 4096 members. In certain embodiments, an AP Endonuclease tail-cleavage assay will use universal oligonucleotide libraries of 6, 7 or 8 nucleotides in length. To increase the hybridization melting temperatures of some or all members of a universal library, the oligonucleotides can contain incorporated modified bases, such as those described above.

D. Microfluidics

Methods for target nucleic acid detection and/or amplification using one or more AP site probes are well suited for large-scale, high-throughput, and parallel processing, particularly when carried out at micro scale volumes, for instance in capillary-design microfluidics devices. Applicable microfluidic devices and systems are commercially available from, for example, Caliper Technologies (Mountain View, Calif., www.calipertech.com) and Aclara Biosciences (Mountain View, Calif., www.aclara.com). Microfluidic devices are applicable for carrying out combined detection and amplification procedures at micro scale volumes. Microfluidic systems and devices of potential use in carrying out the present methods are described, for example, in U.S. Pat. Nos. 6,558,960; 6,551,836; 6,547,941; 6,541,274; 6,534,013; 6,558,945; 6,399,952, 6,306,273; and 6,007,690, and in U.S. Publication Nos. 2003/0027352, 2003/0017467, 2003/17461, 2002/0092767.

The following examples are provided to illustrate, but not to limit, the invention.

IV. EXAMPLES

Example 1

This Example demonstrates the efficacy of an Endonuclease (Class II AP endonuclease) tail-cleavage assay.

Assay Design and Oligonucleotide Component Structures (SEQ ID NOS:3-5):

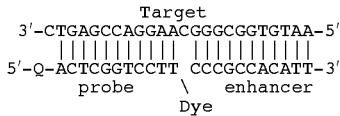

Target
3'-CTGAGCCAGGAACGGGCGGTGTAA-5'
 ||||||||||| |||||||||||
5'-Q-ACTCGGTCCTT CCCGCCACATT-3'
     probe    \    enhancer
              Dye Two probes were used in this example experiment. These probes were designed complementary to a target oligonucleotide and they share the same oligonucleotide structure and a 5'-conjugated quencher (Q) moiety. Structure of the quencher is shown on FIG. 8 (structure #15). First probe was conjugated to a fluorescein dye via a rigid, hydroxyprolinol linker at the 3'-end. Structure of the 3'-tail used (structure #8) is shown on FIG. 7. Second probe contained a flexible endonuclease-cleavable linker that was created by incorporation of an additional, propandiol linker (—O—PO$_2$—O—CH$_2$CH$_2$CH$_2$—O—) between 3'-OH group of the first probe and the hydroxyprolinol linker. An enhancer oligonucleotide was used in the assay to support the tail cleavage reaction. The target has one unpaired base between the duplexes of the probe and enhancer.

The experiment was carried out using an LightCycler™ (Idaho Technology Inc.). Samples were prepared on ice by mixing concentrated component stock solutions and then quickly transferred to the instrument chamber where they were heated to and kept at 40° C. Final concentration of the reaction components: probe=enhancer=150 nM, target=5 nM, E. coli Endonuclease IV=0.04 Units/μL, Bovine Serum Albumin (BSA)=0.025% in 20 mM Tris-HCl (pH8.5), 5 mM MgCl$_2$. The reaction volume was 10 μL. The time of the fluorescence recording cycle was 40 sec.

Figure 11:
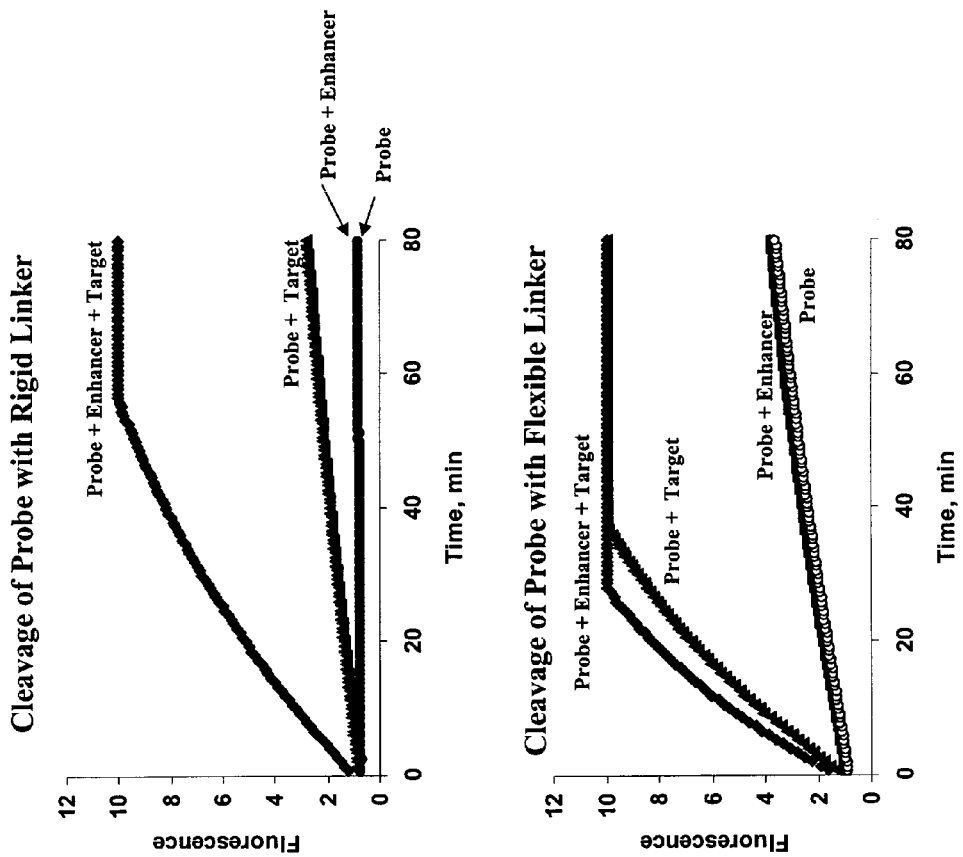
FIG. 11 illustrates the effect of including an enhancer molecule in an AP Endonuclease tail-cleavage assay. The assay is described in Example 1, infra.

The results are depicted in FIG. 11. When probe with the rigid linker is in a mixture with the target and enhancer oligonucleotides, a strong fluorescence signal was detected over the time of the experiment. Endonuclease IV recognized the target-probe-enhancer complex and cleaved the fluorescein-liker moiety of the probe, releasing the dye from the quenching effect of the 5'-Q-tail. Absence of the enhancer resulted in reduction of the signal, whereas removal of the target from the system provided no fluorescence signal at all (background signal), indicating a very high level of the reaction specificity.

When the 3'-endonuclease-cleavable tail was elongated by incorporation of a propandiol linker, the probe with a flexible 3'-tail, similar effects were observed. In contrast to the first probe, the presence of the enhancer was less critical when using the flexible 3'-tail, but fluorescence increase was detected in absence of the target. A high, almost quantitative yield of the target-specific tail-cleavage reaction indicates the cycling mode of the reaction since the probes were taken in 30-fold excess over the target.

Example 2

This Example illustrates that the efficiency of the AP endonuclease tail-cleavage reaction depends on the balance between the hybridization properties of the probes and temperature of the reaction. Probes complementary to target of 11, 9, 7 and 6 nucleic acids in length were prepared.

Assay Design, Component Structures (SEQ ID NOS:3-5) and Melting Temperatures (T$_m$):

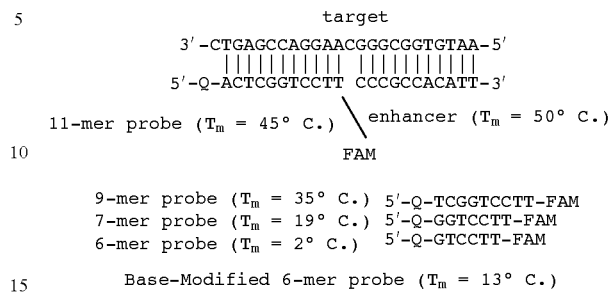

target
3'-CTGAGCCAGGAACGGGCGGTGTAA-5'
   ||||||||||| |||||||||||
5'-Q-ACTCGGTCCTT CCCGCCACATT-3'
11-mer probe (T$_m$ = 45° C.)  \ enhancer (T$_m$ = 50° C.)
                               FAM 9-mer probe (T$_m$ = 35° C.) 5'-Q-TCGGTCCTT-FAM
7-mer probe (T$_m$ = 19° C.) 5'-Q-GGTCCTT-FAM
6-mer probe (T$_m$ = 2° C.)  5'-Q-GTCCTT-FAM Base-Modified 6-mer probe (T$_m$ = 13° C.)

Q is a 5'-conjugated quencher (structure #15) shown on FIG. 8. FAM is an endonuclease cleavable tail comprising of a fluorescein dye and linker that are shown on FIG. 7 (Structure 8). In addition to the shown 6-mer probe, a base-modified 6-mer probe was prepared. All three T bases in this probe were replaced with 5-hydroxybutynyl uridine that provides a duplex stabilizing effect.

Figure 12:
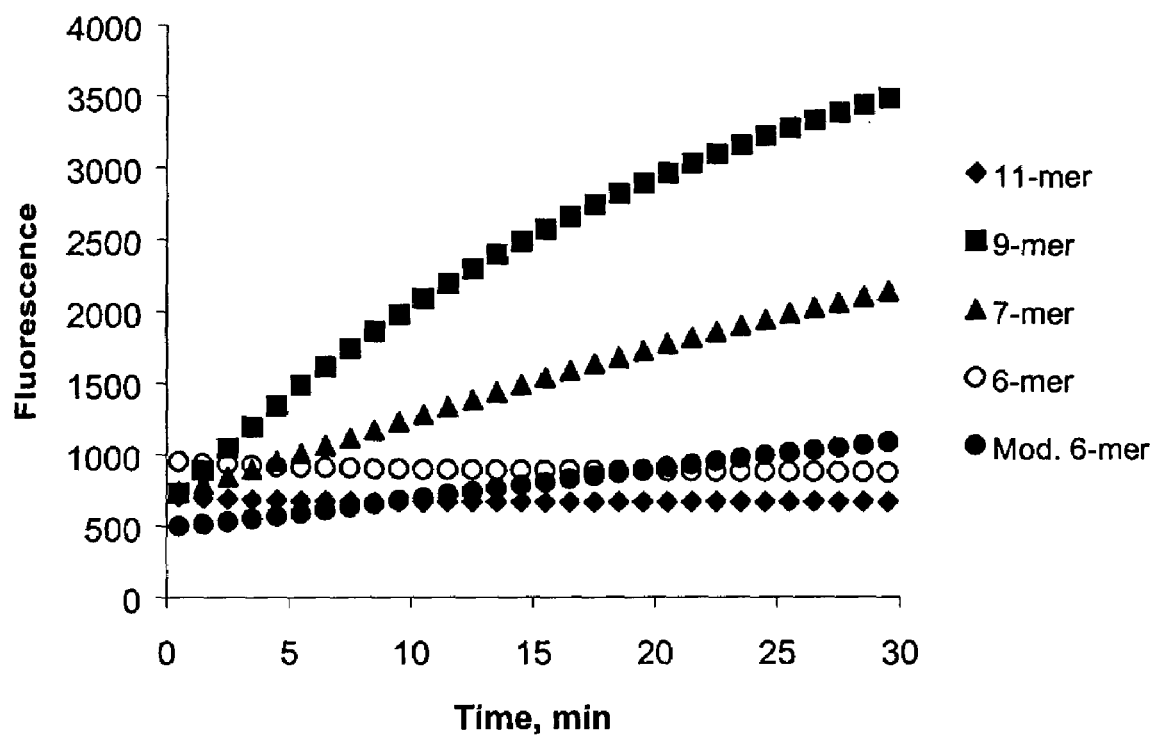
FIG. 12 illustrates the efficiency of the tail-cleavage reaction as a function of probe hybridization properties, i.e., melting temperature ($T_m$). The assay is described in Example 2, infra.

This experiment was done on an ABI PRISM™ 7700 Sequence Detector. The reaction volume was 10 μL. Samples were prepared on ice and then quickly transferred to the instrument chamber where they were heated to and kept at 30° C. The time of the fluorescence recording cycle was 30 sec. Final component concentrations in the samples: probe=enhancer=150 nM, target=5 nM, E. coli Endonuclease IV=0.04 Units/μL in 20 mM Tris-HCl (pH8.5), 5 mM MgCl$_2$. The results are depicted in FIG. 12. The tail of the longest 11-mer probe (T$_m$=45° C.) was not cleaved in the presence of the enhancer and target at 30° C. whereas fluorescence was detected at 40° C. The elevated stability of the duplex formed with the longest probe interferes with the target recycling efficiency. The tail of the shorter 9-mer probe (T$_m$=35° C.) was efficiently cleaved. Efficiency of the target-specific tail-cleavage depends on how the hybridization properties of the probes are balanced with the reaction temperature. Generally, the greater the difference between the probe T$_m$ and reaction temperature, the lower the fluorescent signal over increasing reaction time. Target-specific cleavage of the tail of the 6-mer probe (T$_m$=2° C.) was not observed. However, when the duplex-stabilizing bases were incorporated into this probe (T$_m$=13° C.), fluorescent signal was detected.

Example 3

This Example illustrates the substrate specificity of E. coli Endonuclease IV. In this set of experiments (SEQ ID NOS: 3-7), the enhancer was positioned along the target sequence to provide a gap between the duplexes of the probe and enhancer of 0, 1 or 2 nucleotides.

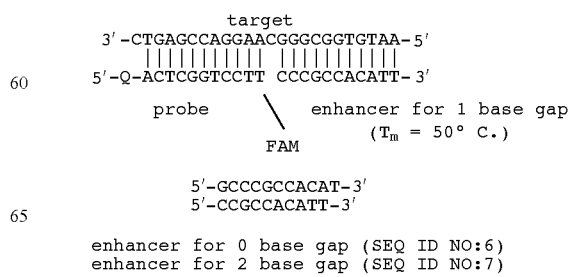

target
3'-CTGAGCCAGGAACGGGCGGTGTAA-5'
   ||||||||||| |||||||||||
5'-Q-ACTCGGTCCTT CCCGCCACATT-3'
     probe       \  enhancer for 1 base gap
                FAM   (T$_m$ = 50° C.)

5'-GCCCGCCACAT-3'
5'-CCGCCACATT-3' enhancer for 0 base gap (SEQ ID NO:6)
enhancer for 2 base gap (SEQ ID NO:7)

Q is a 5'-conjugated quencher (structure #15) shown on FIG. 8. FAM is an endonuclease cleavable tail comprising of a fluorescein dye and linker that are shown on FIG. 7 (Structure 8).

The experiment was done on a Rotor-Gene 3000 (Corbett Research, Sydney, Australia). The reaction volume was 10 μL. Samples were prepared on ice and then quickly transferred to the Rotor-Gene chamber where they were heated to and kept at 40° C. The time of the fluorescence recording cycle was 40 sec. Final component concentrations in the samples: probe=enhancer=150 nM, target=5 nM, *E. coli* Endonuclease IV=0.04 Units/μL in 20 mM Tris-HCl (pH8.5), 5 mM MgCl$_2$.

Figure 13:
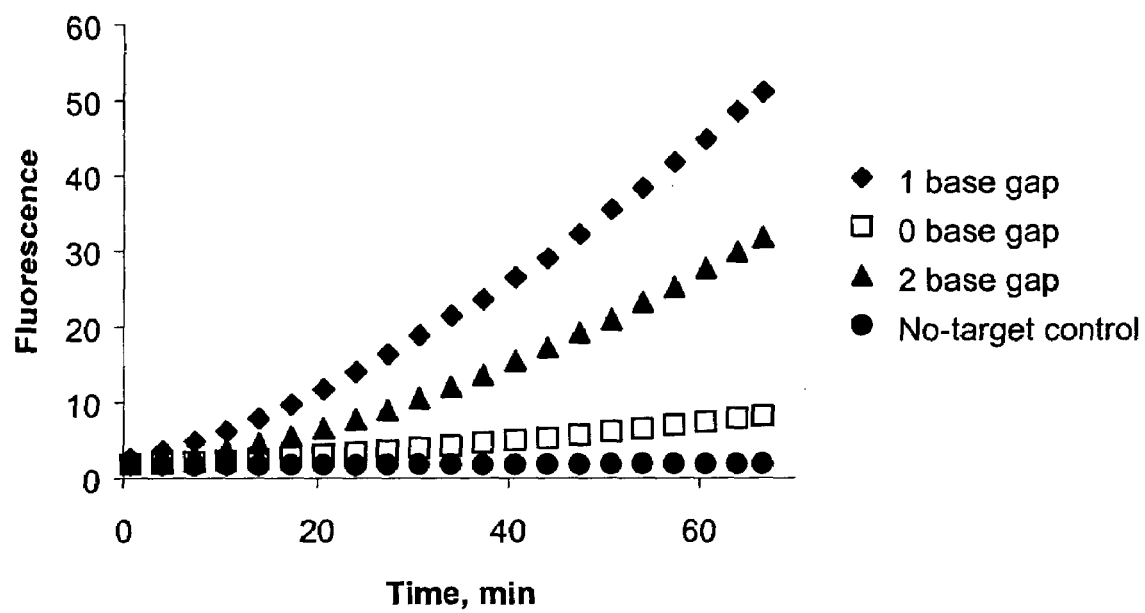
FIG. 13 illustrates substrate specificity of the Endonuclease IV enzyme in the presence of varying gap sizes between the AP site probe and an enhancer molecule. The assay is described in Example 3, infra.

The results are depicted in FIG. 13. The greatest fluorescent signal was observed when a gap of 1 nucleotide was present between the probe and the enhancer hybridized to the target. A probe-target nucleic acid-enhancer complex with no unpaired bases between the probe and enhancer showed little detectable fluorescent signal, presumably due to greatly diminished cleavage of the fluorescent tail. Complexes having a two base gap performed much better than complexes without a base gap. Complexes having a one base gap were the preferred substrate for the Endonuclease IV, most likely because this complex most closely resembles a natural substrate for the enzyme.

Example 4

This Example illustrates the application of the tail cleaving assay to the discrimination of single base pair mismatch. Endonuclease IV discriminates single base-pair mismatches, particularly those located at the 3'-end of AP site probe hybridized with a target nucleic acid.

Assay Design and Oligonucleotide Component Structures (SEQ ID NOS:8-11):

```
                        41-mer target
5'-AGTCACAGTCGGTGCCAATGTGGCGGGCAAGGACCGAGTCG-3'
   ||||||||||||||||||||||||||  ||||||||||||||
3'-AGTGTCAGCCACGGTTACACCG ┌CCGTTCCTGGCTCA-Q-5'
        enhancer      FAM┘     14-mer probe
                                ┌CCGTTCCTGG-Q-5'
                            FAM┘    10-mer probe
```

Figure 14:
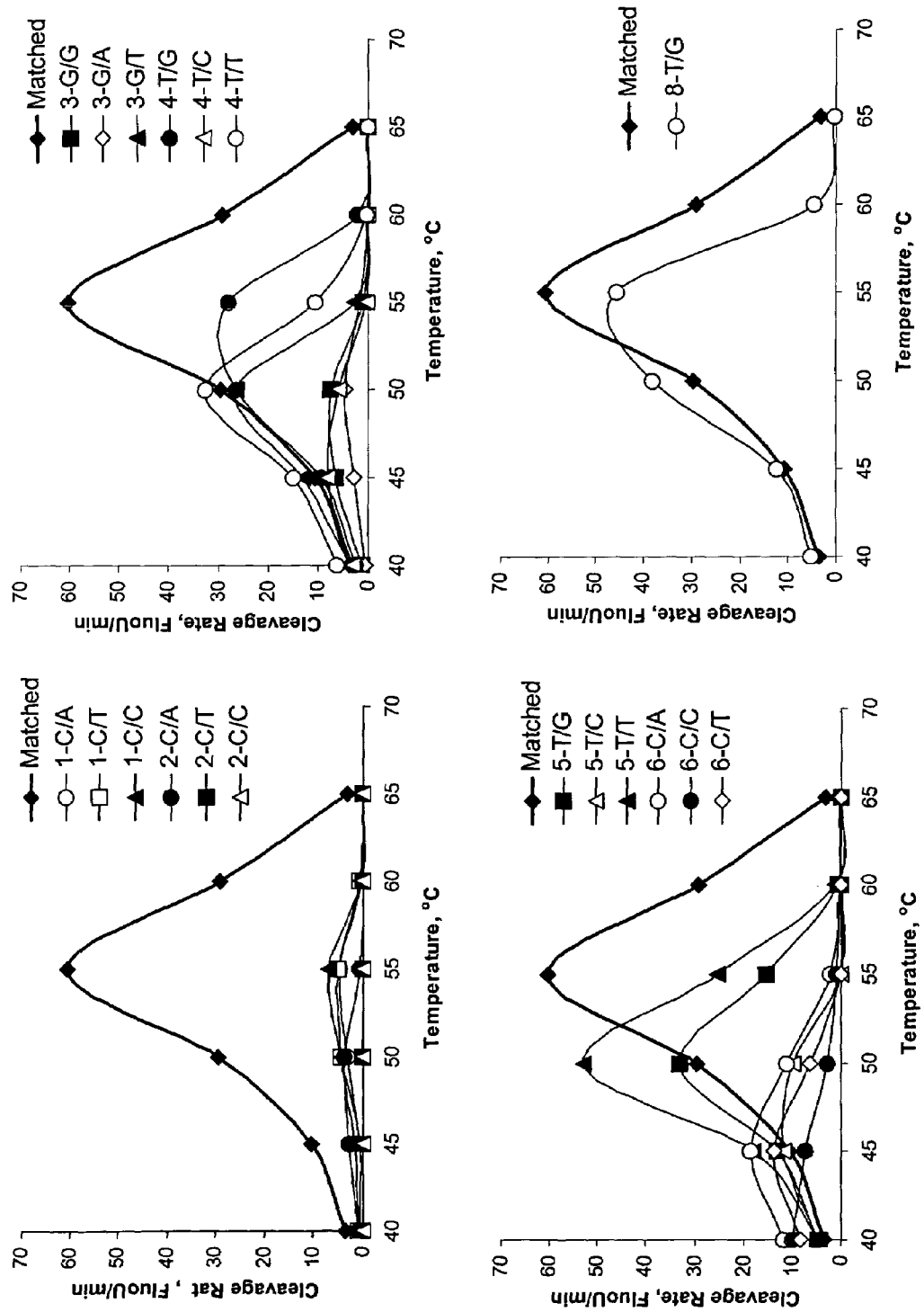
FIG. 14 illustrates the effect of distance of the mismatches from the 3'-end of a hybridized AP site probe on tail cleavage efficiency. The mismatches were placed 1, 2, 3, 4, 5, 6 and 8 bases from the 3' end of a 14-mer probe. Types of single nucleotide mismatches (SNPs) and their positions from the 3'-end of the probe are shown on left of each graph. The assay is described in Example 4, infra.
Figure 15:
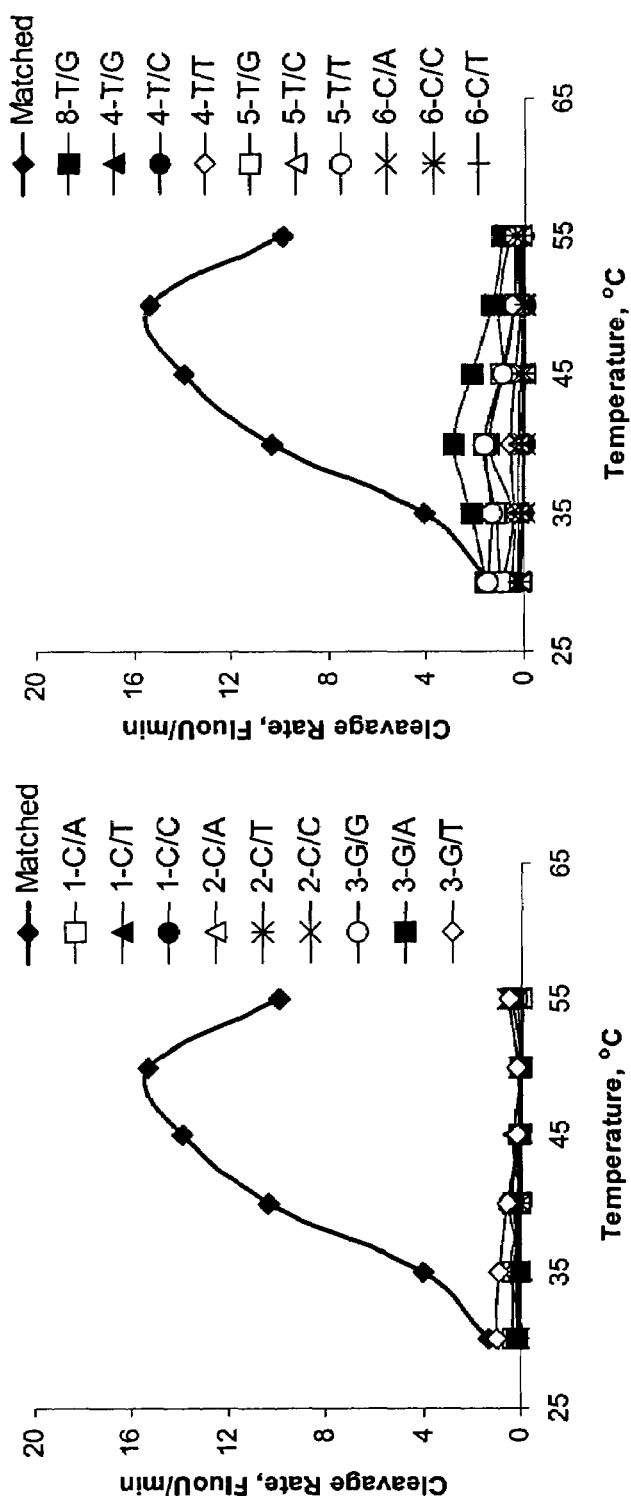
FIG. 15 illustrates the exquisite ability of a relatively short, 10-mer AP site probe to discriminate a single nucleotide polymorphism in a targeted nucleic acid. In contrast to the longer, 14-mer probe, performance of which is shown on FIG. 14, the 10-mer probe discriminates all studied SNPs effectively in a broad temperature range. Position of a mismatch vs. the 3'-end of the probe still has an effect on the probe cleavage efficiency but it is much less pronounced than for the longer, 14-mer probe. The assay is described in Example 4, infra.

Q is a 5'-conjugated quencher (structure #15) shown on FIG. 8. FAM is an endonuclease cleavable tail comprising of a fluorescein dye and linker that are shown on FIG. 7 (Structure 8). The probes used in this example are a 14-mer ($T_m$=60° C.) and 10-mer ($T_m$=48° C.) oligonucleotides. The enhancer does not need to cycle in the reaction and it has an elevated $T_m$ of 70° C. In addition to the target sequence shown above, eighteen 41-mer target nucleic acid sequences were synthesized to study the Endonuclease IV tail-cleavage activity in the presence of mismatched probe/target complexes. These DNA targets differed from the fully matched sequence by one base such that they formed three single base mismatches with every probe nucleotide located within six bases closest to the 3'-end. One target hybridized with the probes provided a G/T mismatch located at the position eight from the 3'-end of the probes. Variable bases within the target sequence are underlined. The reactions were run under standard conditions that are described in the Examples 2-4. The initial rate of tail cleavage was measured for every target nucleic acid/probe combination as a function of the reaction temperature. The data for the 14-mer and 10-mer probes are shown in FIG. 14 and FIG. 15, respectively.

Excellent mismatch discrimination is observed when the mismatch is placed 1 or 2 bases from the 3'-end. Probes shorter than 14-mers may discriminate mismatches more effectively. In other experiments (FIG. 15), a 10-mer probe showed a 4-fold slower rate of the tail cleavage at the optimal reaction temperature, as measured by fluorescence units per minute, in comparison to a 14-mer probe. However, a greater overall range in detectable signal between matched and mismatched duplexes was observed when using a 10-mer probe. Because of the greater thermodynamic contribution of each nucleotide base pair in shorter probes relative to overall duplex energy, shorter probes appear to more effectively discriminate between complementary and mismatched probe-target duplexes.

Both thermodynamic and enzyme efficiency contribute to SNP discrimination in an AP endonuclease tail cleaving assay. With regard to thermodynamics, at a given temperature, probes bind with different efficiencies to the matched and mismatched sites. With regard to enzyme efficiency, the endonuclease cleavage efficiency is decreased when the base pair mismatch is located close to the 3'-end of the probe. The further the mismatch from the 3'-end of the probe, the more diminished effect it had on enzyme tail-cleavage efficiency. Optimal mismatch discrimination was achieved in cases when mismatches were located at the very 3'-end of the probe (position 1) or at the next base pair (position 2). When mismatches are at position 2, fluorescent signal is essentially undetectable.

Stable mismatches like T/G were not as effectively discriminated. In contrast, A/C, T/C, C/C mismatches were discriminated very well. Unexpectedly, a relatively unstable T/T-mismatch at positions 4 and 5 allowed for detectable probe tail-cleavage although the maximum of the probe tail-cleavage occurred at lower temperatures.

Example 5

This Example illustrates the application of the tail cleaving assay for a post-PCR detection of a single nucleotide polymorphism in human genomic DNA using two AP site probes from a universal library 8 nucleotides in length.

Assay Design and Oligonucleotide Component Structures:

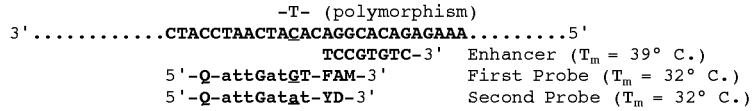

A fragment of the target sequence around the polymorphism is shown above. (SEQ ID NO:12). The T/C mismatch is underlined. First and second probe were labeled with a fluorescent tails that are shown on FIG. 7, structure #8 (FAM) and #7 (YD) respectively. Q is a 5'-conjugated quencher (structure #15) shown on FIG. 8. The A and T bases are substituted with modified bases "a" and "t".

Three individual samples of the human genomic DNA that were prior genotyped as T-homozygous, T/C-heterozygous and C-homozygous at the polymorphism of interest were amplified in an asymmetric PCR. PCR were performed on ABI PRISM™ 7700 Sequence Detector using forward CAAACTTTGTCCTTGGTCTA (SEQ ID NO:13) and reverse TTCTTTTACCACTCCCCCTT (SEQ ID NO:14) primers and a PCR cycling profile: 2 min 50°-2 min 95°-(5 sec 95°-20 sec 56°-30 sec 76°)×50 times.

PCR Reaction Composition and Concentration:

Forward primer—2 µM; reverse primer—100 nM; target DNA—1 mg/µl; JumpStart Taq DNA polymerase—0.08 U/µl; Uracil-N-Glycosylase—0.01 U/µl; dATP, dCTP and dGTP—125 µM; dUTP—250 µM in 40 mM NaCl, 20 mM Tris-HCl (pH8.7), 2.5 mM $MgCl_2$. PCR reaction volume was 50 µl.

Figure 16:
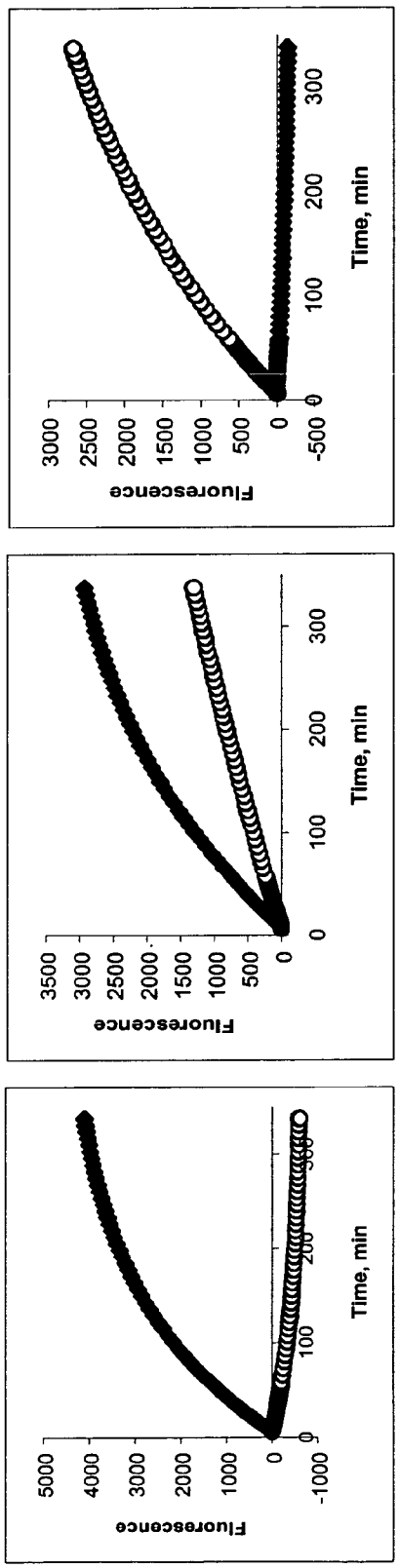
FIG. 16 illustrates post-PCR detection of a single nucleotide polymorphism in human DNA samples with two 7-mer AP site probes labeled by distinguishable fluorescent dyes and containing modified "a" and "t" bases ("a" is Super A™ and "t" is Super T™, see www.Epochbio.com). The assay is described in Example 5, infra.

After 50 cycles, 5 µl of each PCR reaction was mixed with 5 µl of a solution that contained both AP site probes and the enhancer at concentration 300 nM and *E. coli* Endonuclease IV—0.08 U/µl in 40 mM Tris-HCl (pH8.5), 10 mM $MgCl_2$. Reaction mixture were transferred to the ABI PRISM™ 7700 Sequence Detector chamber where they were heated to and kept at 30° C. Fluorescence was detected in FAM and VIC channels of the instrument. Results are shown on FIG. 16. Cleavage of the AP site probes is in agreement with the DNA allelic composition. Only first probe was cleaved in case of C-homozygous DNA and the increase of the fluorescent signal over time was detected in the FAM channel respectively. The situation is reversed when T-homozygous DNA was used whereas both probe were cleaved in the reaction mixture containing the heterozygous DNA amplified.

Example 6

This Example illustrates that cleavage of a functional tail R from an AP site probe does not effect on the probe hybridization properties. Two samples were prepared by mixing a complementary target oligodeoxyribonucleotide 5'-CAAGGACCGAGTC-3' (SEQ ID NO:15) in 5 mM $MgCl_2$, 20 mM Tris-HCl (pH8.5) with ODN probes 5'-Q-ACTCGGTCCTT-FAM-3' (SEQ ID NO:16) and 5'-Q-ACTCGGTCCTT-3'(SEQ ID NO:17) respectively. Q is a 5'-conjugated quencher (structure #15) shown on FIG. 8. FAM is an endonuclease cleavable tail comprising of a fluorescein dye and linker that are shown on FIG. 7 (Structure 8). Denaturation profiles of the duplexes are shown on FIG. 17. These profiles were obtained by monitoring the sample absorbance ($A_{260}$) vs. temperature (0.4° C./min). The target ODN was taken in 1.2 fold excess over the probes that were at 1 µM concentration.

It is understood that the examples and embodiments described herein are for illustrative purposes only and that various modifications or changes in light thereof will be suggested to persons skilled in the art and are to be included within the spirit and purview of this application. All publications, patents, and patent applications cited herein are hereby incorporated herein by reference in their entirety for all purposes.

What is claimed is:

1. A method of detecting a target nucleic acid in a sample, comprising:
   a) contacting the sample with at least one AP site probe and an AP endonuclease, under conditions sufficient to allow the AP site probe to hybridize to the target nucleic acid and form a reaction mixture, wherein said AP site probe comprises an oligonucleotide NA that hybridizes to the target nucleic acid and a functional tail R comprising a detectable reporter group, said functional tail R attached via a phosphodiester bond of a phosphate group to the 3' terminal nucleotide of the NA, wherein the reporter group is not detected when the functional tail R is attached to the NA; and
   b) incubating the reaction mixture under reaction conditions sufficient to allow said AP endonuclease to cleave the phosphodiester bond attaching the functional tail R to the 3' terminal of the NA, wherein the AP endonuclease preferentially cleaves the phosphodiester bond attaching the tail R to the NA when the NA is hybridized with a complementary target nucleic acid sequence in comparison to when the NA is unhybridized or hybridized to a non-complementary target nucleic acid; and
   c) detecting the reporter group on the cleaved functional tail R, whereby the target nucleic acid is detected.

2. The method of claim 1, further comprising contacting the sample with an enhancer oligonucleotide, wherein the 5'-end of said enhancer oligonucleotide hybridizes to the target nucleic acid on the 3' side of the hybridized AP site probe, wherein a gap of 1, 2 or 5 unpaired bases resides between the enhancer oligonucleotide and the AP site probe hybridization locations with the target nucleic acid.

3. The method of claim 2, wherein said AP site probe is covalently linked to the 3' end said enhancer.

4. The method of claim 1, further comprising a quencher molecule attached to the 5' end of the NA of said AP site probe via a non-cleavable linker.

5. The method of claim 1, wherein the cleavage of the phosphodiester bond results in a hybridized NA having a free 3'-OH.

6. The method of claim 5, further comprising contacting the sample with a nucleic acid polymerase, and further comprising amplifying the target nucleic acid, said amplifying comprising incubating the sample under reaction conditions sufficient to allow the polymerase to extend the hybridized NA in a template-specific manner.

7. The method of claim 6, wherein said amplifying is isothermal amplification.

8. The method of claim 5, wherein the sample is incubated under reaction conditions that simultaneously allow the AP endonuclease to cleave the phosphodiester bond of the AP site probe and the polymerase to extend the cleaved AP site probe in a template-specific manner.

9. The method of claim 1, wherein the NA of said AP site probe is 3-200 nucleotides in length.

10. The method of claim 1, wherein the functional tail R is attached to the phosphate group through a hydroxyprolinol linker.

11. The method of claim 1, wherein the reporter group is a fluorophore.

12. The method of claim 1, wherein the AP endonuclease is a Class II AP endonuclease.

13. The method of claim 12, wherein the Class II AP endonuclease is an *E.coli* Endonuclease IV.

14. The method of claim 1, wherein the target nucleic acid is attached to a solid support.

15. The method of claim 1, wherein the AP site probe is attached to a solid support.

16. The method of claim 2, wherein the enhancer is attached to a solid support.

17. The method of claim 1, wherein step (a) further comprises contacting a second AP site probe with the target nucleic acid, wherein said first probe comprises a NA portion comprising at least one base difference from the NA portion of said second probe, and wherein said first probe comprises a reporter group that is distinguishably detectable from the reporter group of said second probe.

18. The method of claim 17, wherein the reporter group of said first probe and said second probe comprises a fluorophore, and wherein the fluorophore of said first probe comprises a distinguishably detectable emission wavelength from the fluorophore of said second probe.

19. The method of claim 17, wherein said at least one base difference between the NA of said first probe and the NA of said second probe comprises a base difference at position 1, 2, 3 or 4 from the 3' end of said probes.

20. The method of claim 17, wherein said at least one base difference between the NA of said first probe and the NA of said second probe comprises a base difference at position 1 or 2 from the 3' end of said probes.

21. The method of claim 1, wherein said at least one AP site probe comprises a plurality of AP site probes, wherein the NA portion of said probes are members of a universal library.

22. The method of claim 21, wherein the NA portion of said AP site probe members is 5-8 nucleotides in length.

23. The method of claim 9, wherein said AP site probe members further comprise at least one modified base.

24. A method of detecting a target nucleic acid in a sample, comprising:
   a) contacting the sample with at least one AP site probe and an AP endonuclease, under conditions sufficient to allow the AP site probe to hybridize to the target nucleic acid and form a reaction mixture, wherein said AP site probe comprises an oligonucleotide NA that hybridizes to the target nucleic acid, a functional tail R comprising a quencher molecule, said functional tail R attached via a phosphodiester bond of a phosphate group to the 3' terminal of the NA, and a reporter group attached via a non-cleavable linker to the 5' terminal of the NA, wherein the reporter group is not detected when the functional tail R is attached to the NA; and
   b) incubating the reaction mixture under reaction conditions sufficient to allow said AP endonuclease to cleave the phosphodiester bond attaching the functional tail R to the 3' terminal of the NA, wherein the AP endonuclease preferentially cleaves the phosphodiester bond attaching the tail R to the NA when the NA is hybridized with a complementary target nucleic acid sequence in comparison to when the NA is unhybridized or hybridized to a non-complementary target nucleic acid; and
   c) detecting the reporter group upon cleavage of the functional tail R, whereby the target nucleic acid is detected.

25. The method of claim 1, wherein said target nucleic acid is a product of an amplification reaction.

26. The method of claim 25, wherein said amplification reaction is polymerase chain reaction.

27. The method of claim 25, wherein said amplification reaction is polymerase chain reaction and said method uses thermostable endonuclease.

28. The method of claim 25, wherein said amplification reaction is an isothermal amplification reaction.

* * * * *